United States Patent
Marchal et al.

(10) Patent No.: US 8,414,865 B2
(45) Date of Patent: Apr. 9, 2013

(54) **USE OF *MYCOBACTERIUM BOVIS* BCG KILLED BY EXTENDED FREEZE DRYING (EFD) FOR PREVENTING OR TREATING ATHEROSCLEROSIS**

(75) Inventors: Gilles Marchal, Paris (FR); Micheline Lagranderie, Neuilly sur Seine (FR); Isabelle Schwartz-Cornil, Jouy en Josas (FR)

(73) Assignees: Institut Pasteur, Paris (FR); Institut National de la Recherche Agronomique, Paris (FR)

( * ) Notice: Subject to any disclaimer, the term of this patent is extended or adjusted under 35 U.S.C. 154(b) by 0 days.

(21) Appl. No.: 13/389,929

(22) PCT Filed: Aug. 12, 2010

(86) PCT No.: PCT/IB2010/053652
§ 371 (c)(1),
(2), (4) Date: Apr. 19, 2012

(87) PCT Pub. No.: WO2011/018769
PCT Pub. Date: Feb. 17, 2011

(65) Prior Publication Data
US 2012/0201856 A1    Aug. 9, 2012

(30) Foreign Application Priority Data
Aug. 13, 2009   (EP) .................................... 09290627

(51) Int. Cl.
A61K 49/00    (2006.01)
A61K 39/04    (2006.01)
A61N 63/00    (2006.01)

(52) U.S. Cl. ........ 424/9.2; 424/9.1; 424/93.1; 424/93.4; 424/248.1

(58) Field of Classification Search .................. 424/9.1, 424/9.2, 93.1, 93.4, 248.1; 34/284; 426/384
See application file for complete search history.

(56) References Cited

FOREIGN PATENT DOCUMENTS

| WO | 00/74715 | 12/2000 |
| WO | 03/049752 | 6/2003 |
| WO | 2007/072230 | 6/2007 |

OTHER PUBLICATIONS

Mendez-Samperio, *Mycobacterium bovis* Bacillus Calmette-Guerin (BCG) Stimulates IL-10 Production via the PI3K/Akt and p38 MAPK Pathways in Human Lung Epithelial cells, Cellular Immunology, 251, pp. 37-42, 2008.

Nilsson, Autoimmunity in Atherosclerosis: A Protective Response Losing Control?, Journal of Internal Medicine, 263, 464-478, 2008.

*Primary Examiner* — Rodney P. Swartz
(74) *Attorney, Agent, or Firm* — Morgan, Lewis & Bockius LLP

(57) ABSTRACT

Use of *Mycobacterium bovis* BCG killed by Extended Freeze Drying (EFD) for preventing or treating atherosclerosis.

10 Claims, 35 Drawing Sheets

…

Figure 1:
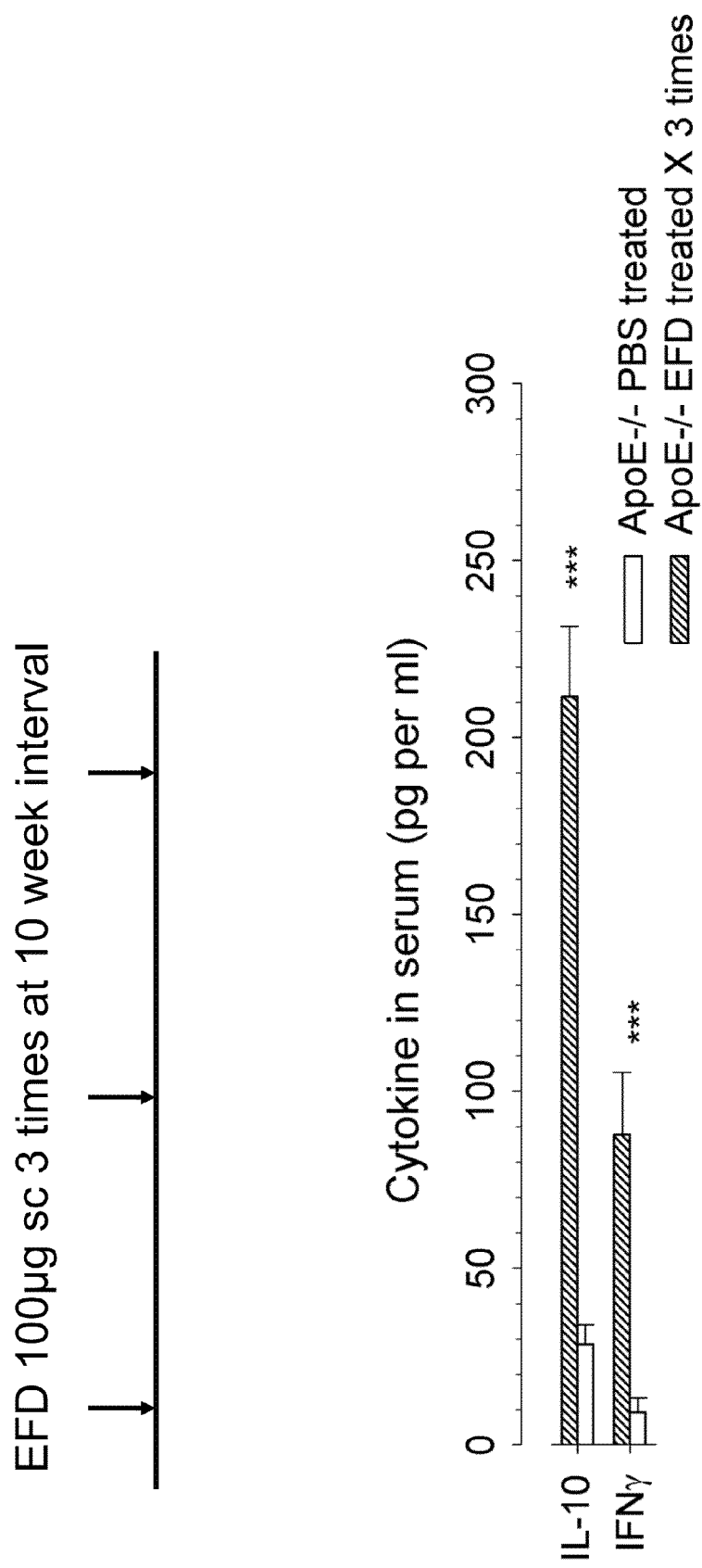
Figure 2:
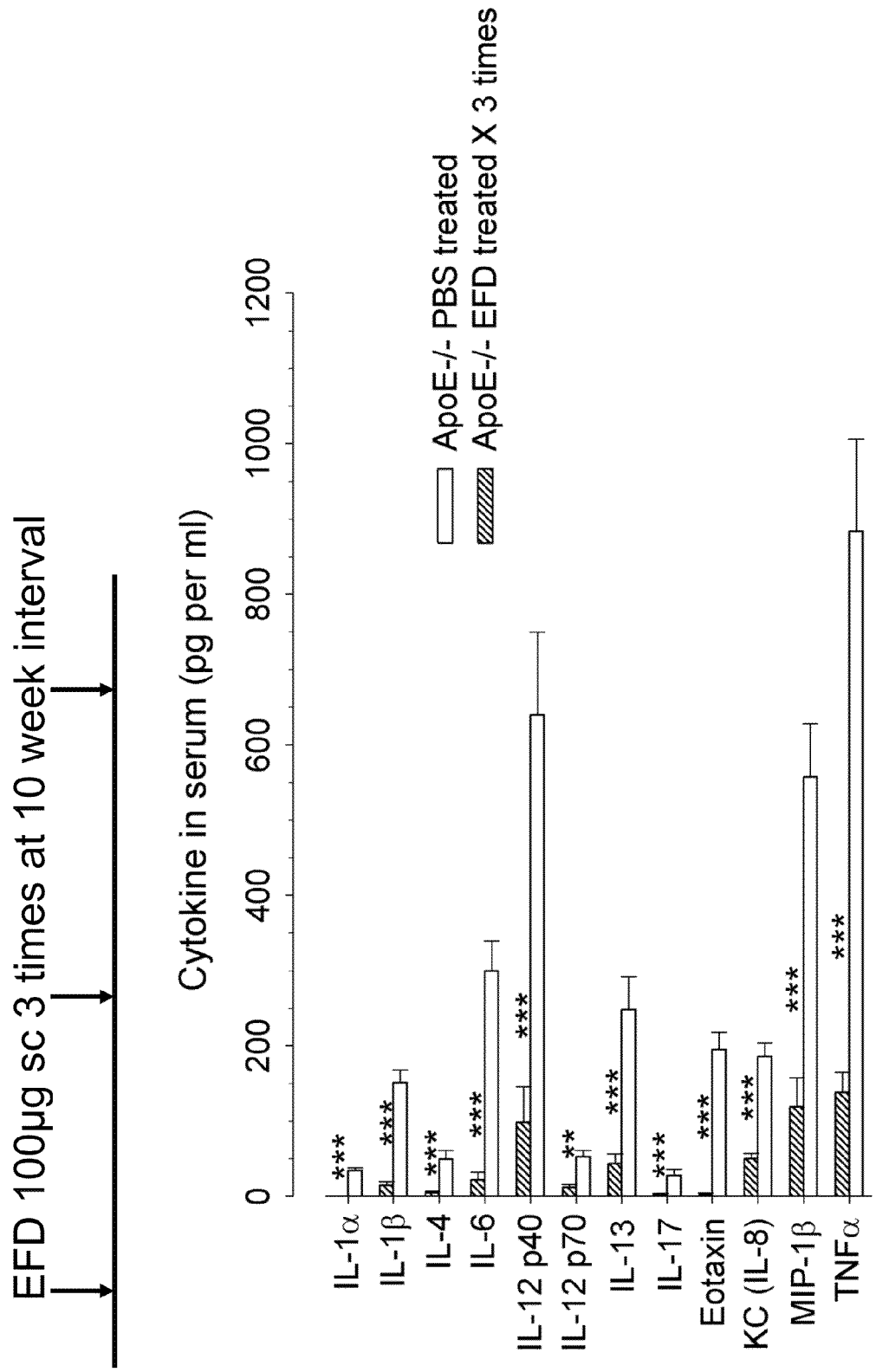

USE OF *MYCOBACTERIUM BOVIS* BCG KILLED BY EXTENDED FREEZE DRYING (EFD) FOR PREVENTING OR TREATING ATHEROSCLEROSIS

RELATED APPLICATIONS

The present application is a U.S. National Phase Application of International Application No. PCT/IB2010/053652 (filed Aug. 12, 2010) which claims priority to European Application No. 09290627.0 (filed Aug. 13, 2009) which are hereby incorporated by reference in their entirety.

The invention relates to the use of *Mycobacterium bovis* BCG killed by Extended Freeze Drying (EFD) for preventing or treating atherosclerosis.

Atherosclerosis is a complex chronic inflammatory process that progresses over decades. It is characterized by the accumulation of oxidized low-density lipoproteins (LDL), increased cell death and hypertrophic degeneration of the arterial wall, causing narrowing of the channel and thus impairing blood flow. It can occur in any area of the body, but is most important when it happens in the heart, brain or blood vessels leading to the brain. The narrowing is due to the formation of plaques (raised patches) in the inner lining of the arteries. These plaques consist of low-density lipoproteins, decaying muscle cells, fibrous tissue, clumps of blood platelets, cholesterol, macrophages, T-lymphocytes and sometimes calcium. They tend to form in regions of turbulent blood flow and are found most often in people with high concentrations of cholesterol in the bloodstream. The number and thickness of plaques increases with age, causing loss of the smooth lining of the blood vessels and encouraging the formation of thrombi (blood clots). Sometimes fragments of thrombi break off and form emboli, which travel through the bloodstream and block smaller vessels.

Atherosclerosis and its clinical manifestations are a major cause of morbidity and mortality among both men and women. Atherosclerotic heart disease, involving the coronary arteries (coronary heart disease), is the most common cause of death, accounting for one-third of all deaths. Atherosclerotic interference with blood supply to the brain (stroke) is the third most common cause of death after cancer. Vascular insufficiency is another clinical manifestation of atherosclerosis which causes a great deal of serious illness by reducing the flow of blood in other major arteries, such as to the kidneys, legs, and intestines.

Unfortunately, atherosclerosis produces no symptoms until the damage to the arteries is severe enough to restrict blood flow. Restriction of blood flow to the heart muscle due to atherosclerosis can cause angina pectoris or a myocardial infarction (a heart attack). Restriction of blood flow to the muscles of the legs causes intermittent claudication (pains in the legs brought about by walking and relieved by rest). Narrowing of the arteries supplying blood to the brain may cause transient ischemic attacks (symptoms and signs of a stroke lasting less than 24 hours) and episodes of dizziness, or ultimately, to a stroke itself.

Current medical treatment of atherosclerosis includes the use of several drugs such as Statins (rosuvastatin) and fibrates. Besides anticoagulant drugs used to try to minimize secondary clotting and embolus formation, vasodilator drugs provide symptom relief but are of no curative value. Surgical treatment is available for those unresponsive to medical treatment or in certain high-risk situations. Balloon angioplasty can open up narrowed vessels and promote an improved blood supply. The blood supply to the heart can also be restored by coronary artery bypass surgery. Large atheromatous and calcified arterial obstruction can be removed by endarterectomy, and entire segments of diseased peripheral vessels can be replaced by woven plastic tube grafts.

The pathogenesis of atherosclerosis involves a complex interplay of inflammation, autoimmunity and tissue-specific degeneration.

Multiple risk factors for atherosclerosis include hypertension (high blood pressure), smoking, diabetes mellitus, dyslipidaemia (hypercholesterolemia), metabolic syndrome, obesity, ischemia, male gender, age, family history of heart disease, and a sedentary lifestyle.

Whatever the factors, the resulting chronic inflammation of the arterial intima is the principal driving force behind the development of atherosclerosis. The major cellular processes involved in atherosclerosis include activated endothelial cells which release chemokines. Oxidized low-density lipoproteins (LDL) induce activated endothelial cells to express glycoprotein adhesion molecules (vascular cell adhesion molecule-1 (VCAM-1), intracellular cell adhesion molecule-1 (ICAM-1) and E-selectin) that aid in the recruitment and infiltration of inflammatory cells. After binding to the endothelium, leucocytes infiltrate into the intima. There, monocytes differentiate into macrophages, which sequester cholesterol from oxidized LDL and thereby become foam cells. The resulting accumulation of fatty streaks upon the arterial wall is followed by the formation of advanced atherosclerotic lesions. Vascular smooth muscle cell proliferate and migrate toward the lesion. Upon their recruitment, vascular smooth muscle cells secrete extracellular matrix that forms a fibrous plaque over the lipid atheroma. Ultimately, unstable plaques may rupture, as a result of ongoing chronic inflammation. The resulting thrombi are responsible for acute coronary events such as myocardial infarction and stroke.

NF-κB is a relevant marker associated with activation of inflammatory responses in atherosclerotic lesions (Bank et al., J. Clin. Invest., 1996, 97, 1715-1722), whereas PPARγ signaling inhibits the production of inflammatory cytokines (Jiang et al., Nature, 1998, 391, 82-86). The phosphorylation of I-κB activates NF-κB playing a role in this disease process. However, there is no direct evidence that NF-κB activation is necessary for atherosclerosis (T. Collins and M. I Cybulsky, J. Clinical Investigation, 2001, 107, 255-262). The mitogen-activated protein kinase (MAPK) pathway phosphorylates retinoid X receptor α (RXRα) whereas unphosphorylated RXRα forms a heterodimer with PPARγ to reduce inflammation synergistically (Yamazaki et al., Gut, 2007, 56, 1557-1563).

Targeting the inflammation represents an approach for developing treatments for atherosclerosis. Some anti-inflammatory drugs were shown to exert cardioprotective effects at key stages of atherogenesis. Thiazolinediones are peroxisome proliferator-activated receptor PPARγ agonists that are in clinical use for the treatment of type 2 diabetes. PPARγ regulates numerous cellular processes contributing to atherosclerosis. In vitro animal model and clinical studies indicate that thiazolinediones correct endothelial dysfunction, suppress chronic inflammatory processes, reduce fatty streak formation, delay plaque evolution and vessel wall thickening and enhance plaque stabilization. Thus thiazolinediones show potential as anti-inflammatory, antithrombic agents that could both improve glucose levels and the long-term cardiovascular risk related to atherosclerosis in patients with type 2 diabetes (B. Staels, Current Medical Research and Opinion, 2005, 21, suppl 1, S13-S20). However, the combination of PPARγ agonists (used as insulin sensitizers in diabetic patients who are at high risk for cardiovascular disease) and of PPAR-α agonists (used to treat dyslipidemia) enhanced atherosclerosis in ApoE−/− (Calkin et al., Atherosclerosis, 2007, 195, 17-22) and induced major adverse cardiovascular events in humans (Nissen et al., JAMA, 2005, 294, 2581-2586).

More recently, an increasing body of evidence suggests that the immune system is a major factor modulating the atherogenic process (for a review see Nilsson, J. and G. K. Hanson, Journal of Internal Medecine, 2008, 263, 464-478). Although most inflammatory cells in atherosclerotic lesions are macrophages, up to 20% of the cells are T lymphocytes (Hansson, G. K., N. Engl. J. Med., 2005, 352, 1685-1695). The disease process is associated with local formation of modified self antigens (oxidized LDL, HSP, apoptotic fragments) that are targeted by both innate and adaptative immune responses. It is likely that these autoimmune responses have a beneficial effect facilitating the removal of potentially harmful rest products from oxidized LDL and dying cells. However, if the balance between protective and disease-promoting autoimmunity is lost, the autoimmune system may accelerate into a destructive pro-inflammatory process causing plaque growth and destabilization. These observations point to the possibility of developing new treatments for atherosclerosis based on modulation of immune responses against plaque antigens.

Animal studies have provided proof-of-principle support that it is possible to inhibit the development of atherosclerosis by modulating immune responses against plaque antigens by vaccines based on antigens present in oxidized LDL. However, as oxidized LDL is a complex particle with an antigen composition that it is difficult to standardize and as it potentially may also contain harmful antigens it is in itself not an ideal vaccine component. Over the last few years considerable effort has therefore been put on characterizing the exact antigens in oxidized LDL that induce athero-protective immunity. Two antigens were identified in oxidized LDL: oxidized phospholipids (phosphorylcholine) and apo B-100 peptides (Klingenberg et al., Arterioscler. Thromb. Vasc. Biol., 2010, 30, 946-952). A limitation with both phosphorylcholine and apo B peptide-based vaccines, is that the mechanism of action is poorly understood. Oxidized phospholipids are recognized by a subclass of IgM referred to as natural antibodies, whose regulation of expression is poorly understood, and which cross-react with self antigens associated with senescent cells and cellular debris. The high specificity and the possibility of producing standardized vaccine preparations are some advantages of apo B peptide-based vaccines and human vaccines are presently in preclinical development. The disadvantages with this approach include the need for human leucocyte antigen (HLA) genotyping of patient before treatment and the risk that the vaccines need to be individualized depending on HLA type.

However, besides the apo B peptide-based vaccines, no other therapeutic approach targeting the immune system has been developed for the treatment of atherosclerosis, so far.

There are several ways for the body to control the activity of the autoimmune responses, an important one being the regulatory T cells (Tregs). Several subtypes of Tregs have been identified. Natural $CD4^+$ $CD25^+$ $Foxp3^+$ Tregs are developed in the thymus and then enter peripheral tissues where they constitute 5-10% of all T cells. In contrast to natural Tregs, the IL-10-producing T regulatory 1 (Tr1) and TGF-β-producing T helper 3 (Th3) cells are generated from naïve T cells in the periphery following antigen presentation and activation by dendritic cells (DCs). Several lines of evidence have implicated dysregulation of Treg function in atherosclerosis. There is also accumulating functional evidence for a protective role of Tregs in atherosclerosis. Depletion of natural Tregs through deletion of CD80/86, CD28 or ICOS as well as anti-CD25 antibody treatment significantly increases plaque formation (Ait-Oufella et al., Nat. Med., 2006, 12, 178-180; Gotsman et al., Circulation, 2006, 114, 2047-2055). Similarly, inhibition of Th3 cells through deletion of the T-cell receptor for TGF-β markedly enhances the progression of the disease (Roberson et al., J. Clin. Invest., 2003, 112, 1342-1350) whilst administration of a clone of ovalbumin-specific Tr1 cells together with its cognate antigen inhibited plaque development in Apolipoprotein E deficient ($ApoE^{-/-}$) mice (Mallat et al., Circulation, 2003, 108, 1232-1237). However, the understanding of the role of regulatory T cells in atherosclerosis is still very incomplete.

These findings have raised the possibility that immune regulatory pathways can be triggered to reduce inflammation and treat or prevent atherosclerosis. Interestingly, Mycobacterium bovis BCG (Bacille Calmette-Guérin) vaccination was shown to protect against the development of atopy in infants, suggesting that BCG can prevent dysregulation of immune responses (Shirakawa et al., Science, 1997, 275, 77-79)). To circumvent the unfeasible delivery of live BCG as an antiinflammatory treatment, BCG has been killed by Extended Freeze-Drying (EFD BCG or EFD) which has been shown to be a potent anti-inflammatory agent in several animal models of allergy (asthma; International PCT Application WO 03/049752; Lagranderie et al., J. Allergy Clin. Immunol., 2008, 121, 471-478; Lagranderie et al., The Journal of Immunology, 2010, 184, 1062-1070) and intestinal inflammatory disease (inflammatory bowel disease; International PCT Application WO 2007/072230). EFD does not cause the toxic side effects associated with live or heat-killed BCG and does not interfere with the diagnosis of tuberculosis by the DTH skin-test. EFD has the original property of acting not only on the Th1 signalization pathway to which TNF-α, IL-12, IFN-γ and T-bet are associated, but also on the Th2 signalization pathway to which IL-4, IL-13 and GATA-3 are associated and on a new signalization pathway to which IL-17 and PPARγ seem to be associated with (International PCT Application WO 2007/072230). The protective/curative effect of EFD against the symptoms of allergy and intestinal inflammatory disease is associated with the stimulation of CD4+ CD25+ regulatory cells producing IL-10 (International PCT Applications WO 03/049752 and WO 2007/072230).

However, there are major side effects that may be associated with the use of regulatory T cells stimulating agents for treating autoimmune diseases like atherosclerosis (Nilsson, J. and G. K. Hanson, Journal of Internal Medecine, 2008, 263, 464-478). If regulatory T cells are too suppressive, and the immunosuppression is not restricted to the affected tissue, there is a risk that the defense against infections and the CD8 T-cell dependent tumour cell surveillance will be impaired. For example, a viral nucleoprotein derived from measles virus has been shown to reduce atherosclerosis in mice when injected weekly (Ait-Oufella et al., Circulation, 2007, 116, 1707-1713). However, this nucleoprotein triggered the development of suppressive Tregs that secreted IL-10 upon in vitro stimulation and its administration in mice reduced IL-4 and IFN-γ production by T cells, suggesting that the measle nucleoprotein treatment might be immunosuppressive.

The inventors have demonstrated that EFD BCG reduces atherosclerosis in three distinct mouse models: 1) Apolipoprotein E deficient ($ApoE^{-/-}$) mice which spontaneously develop advanced atherosclerosis lesions in 30 weeks; 2) low-density lipoprotein receptor deficient ($Ldlr^{-/-}$) mice which develop atherosclerosis upon hyperlipidemic diet, and 3) $ApoE^{-/-}$ ×CD4dnTβRII mice, which lack functional TGF-β receptors on T cells and spontaneously develop atherosclerosis lesions at 12 weeks.

EFD BCG significantly reduced the size of atherosclerotic lesions in the three atherosclerosis-prone mouse models independently of the targeted gene and TGF-β signaling.

EFD BCG elicited simultaneously: 1) an immunoregulatory effect through IL-10 production and an expansion of Tregs, 2) an inhibition of NF-κB activation, and 3) an increase in PPARγ without altering PPAR-α levels.

That EFD BCG is a selective inducer of PPARγ and does not induce PPARα activation is an advantage, supporting its potential for clinical use.

Unexpectedly, despite its immunoregulatory activity, EFD BCG did not attenuate protection conferred by vaccines generating Th1 and Th2 immune responses (*Neisseria meningitides*, BCG), nor did it exacerbate the course of a pathogen infection (virus (influenza virus), bacteria (*M. tuberculosis*) or parasite (*Leishmania major*)). The maintenance of an efficient immunocompetence of the host suggests that EFD BCG is a tolerable therapeutic agent in humans.

An immunoregulatory profile, without signs of immunosuppression, is induced in response to EFD BCG. The modulated systemic inflammatory profile in the EFD BCG-treated mice was also associated to a reduced local accumulation of MOMA$^+$ macrophages in the plaques, what may also prevent plaque rupture, the highest danger in atherosclerotic disease.

Moreover, EFD BCG had no measurable side effects in this study.

These results indicate that EFD is a new therapeutic approach for the prevention and the treatment of atherosclerosis. EFD is expected to have a prolonged duration of activity (at least 2 months). Therefore, EFD should have the advantage of a very limited number of administration compared to currently used drugs which require daily repetitive administration. In addition, EFD treatment is safe since it does not induce immunosuppression.

The invention relates to the use of *Mycobacterium bovis* BCG bacteria killed by extended freeze-drying (EFD) for preventing or treating atherosclerosis.

The expression "EFD", "EFD BCG" or "extended freeze-dried *Mycobacterium bovis* BCG", as used in the context of the present invention, refers in other words to killed and non-denatured *Mycobacterium bovis* BCG bacteria. In the context of the present invention, non-denatured means that the structure of the *Mycobacterium bovis* BCG bacteria molecules and in particular the primary structure of the macromolecules (proteins, polysaccharides, lipids) is preserved. Preferably, the primary structure of the proteins is preserved. An example of a preserved protein in EFD is Apa, which has the same migrating characteristics in a SDS-PAGE gel as the protein extracted from living BCG (Laqueyrerie et al., Infect. Immun., 1995, 63, 4003-4010). The EFD may be prepared by extended freeze-drying or any other process which kills the bacteria while preserving the structure of its macromolecular components. Preferably, such process preserves the primary structure of the macromolecules from the bacteria cells. These processes which may be used for preparing EFD are known to those of ordinary skill in the art and include the use of physical means, such as for example, extended freeze-drying, grinding in the presence of silica or zirconium beads, use of the so-called "French-press" and sonication.

A fraction of EFD as described above is covered by the expression "EFD" of the invention. This fraction is selected from the group consisting of: a residue from the treatment of EFD with a glycosidase (deglycosylated residue), a residue from the digestion of EFD by a DNase and/or a RNase, a residue from the treatment of EFD with a protease, a residue from the treatment of EFD with successively, a glycosidase, a DNase and/or a RNase, and finally a protease, and a residue from the treatment of said EFD with a protease (as substilisine for example) and a DNase.

According to a preferred embodiment of the invention, the EFD consist of killed and non-denatured *Mycobacterium bovis* BCG bacteria containing less than 1.5% of water, preferably less than 1% of water, more preferably, less than 0.5% of water.

According to another preferred embodiment of the invention, the EFD is prepared according to the method as described in the International PCT Application WO 03/049752, incorporated herein by reference, said method comprising the steps of: (i) harvesting a culture of living bacteria cells, (ii) freezing the bacteria cells in water or in an aqueous solution of a salt, (iii) killing the frozen bacteria cells by drying them in a lyophilizer, for a time sufficient to remove at least 98.5% of the water, preferably at least 99% of the water, more preferably at least 99.5% of the water, and (iv) collecting the extended freeze-dried killed bacteria cells. Optionally, a step of washing of the bacteria cells in water or in an aqueous solution of a salt may be introduced between steps (i) and (ii).

All the fractions of EFD are obtained by resuspending the extended freeze-dried bacteria in water or any hydrophilic solvent and applying the treatment. A classical freeze-drying could be applied to fractions after, for a facilitated storage.

According to another advantageous embodiment of the invention, said EFD is included in a pharmaceutical composition for preventing or treating atherosclerosis further comprising a pharmaceutically acceptable carrier and/or an additive and/or an immunostimulant and/or an adjuvant.

Any suitable carrier known to those of ordinary skill in the art may be employed in the pharmaceutical composition of the present invention, the type of carrier varying depending on the mode of administration. For parenteral administration, such as subcutaneous injection, the carrier preferably comprises water, saline buffer, lactose, mannitol, glutamate, a fat or a wax and the injectable pharmaceutical composition is preferably an isotonic solution (around 300-320 milliosmoles). For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g. polylactic galactide) may also be employed as carriers for the pharmaceutical compositions of this invention. Suitable biodegradable microspheres are disclosed, for example in U.S. Pat. Nos. 4,897,268 and 5,075,109. The additive may be chosen among antiaggregating agents, antioxidants, dyes, flavor enhancers, or smoothing, assembling or isolating agents, and in general among any excipient conventionally used in the pharmaceutical industry. Any of the variety of adjuvants/immunostimulants may be employed in the compositions of the present invention to enhance the immune response. Most adjuvants contain a substance designed to protect the antigen from rapid catabolism or to create controlled inflammatory reactions, such as aluminium hydroxide and a non-specific stimulator of immune response. Suitable adjuvants for human administration are commercially available as, for example, aluminum hydroxide, biodegradable microspheres, monophosphoryl A and Quil A.

The pharmaceutical composition may be in a form suitable for oral administration. For example, the composition is in the form of tablets, ordinary capsules, gelatine capsules or syrup for oral administration. These gelatine capsules, ordinary capsules and tablet forms can contain excipients conventionally used in pharmaceutical formulation, such as adjuvants or binders like starches, gums and gelatine, adjuvants like calcium phosphate, disintegrating agents like cornstarch or algenic acids, a lubricant like magnesium stearate, sweeteners or flavourings. Solutions or suspensions can be prepared in aqueous or non-aqueous media by the addition of pharmacologically compatible solvents. These include glycols, polyglycols, propylene glycols, polyglycol ether, DMSO and ethanol.

In general, the composition may be administered by parenteral injection (e.g., intradermal, intramuscular, intravenous or subcutaneous), intranasally (e.g. by aspiration or nebulization), orally, sublingually, or topically, through the skin or through the rectum epithelium.

The amount of EFD present in the composition of the present invention is a therapeutically effective amount. A therapeutically effective amount of EFD is that amount necessary so that the EFD performs its role of reducing the signs of atherosclerosis without causing overly negative effects in the subject to which the composition is administered. The exact amount of EFD to be used and the composition to be administered will vary according to factors such as the species (human, animal) being treated, the type of subject (subject at risk of atherosclerosis such as dyslipidemia, metabolic syndrome, type 2 diabetes subjects), the mode of administration, the frequency of administration as well as the other ingredients in the composition.

Preferably, the composition comprises from about 10 μg to about 10 mg and more preferably from about 100 μg to about 1 mg, of EFD. By "about", it is meant that a slightly lower or higher quantity of EFD can be used.

For instance, for parenteral administration, such as subcutaneous injection, the individual to be treated could be subjected to a 1 dose schedule of from about 10 μg to about 10 mg and more preferably from about 100 μg to about 1 mg, for example 100 μg of EFD, every week, every month or every 3 to 6 months.

The composition may be used either for preventing atherosclerosis in patients previously diagnosed of atherosclerosis, patients at high risk of atherosclerosis or patients presenting xanthoma and in particular patients presenting xanthelasma or for curing atherosclerosis in patients at the beginning of an episode of atherosclerosis.

The invention also relates to products containing EFD as defined in the invention or fractions thereof and a second product which is different from the first one, said second product being selected from the group consisting of anti-inflammatory and immunomodulatory drugs (acetylsalicylic acid or thiazolidinediones (glitazone), for example), as a combined preparation for simultaneous, separate or sequential use in the prevention and/or the treatment of atherosclerosis.

The invention relates also to the use of *Mycobacterium bovis* BCG bacteria killed by extended freeze-drying (EFD) for the manufacture of a medicament for preventing or treating atherosclerosis, as defined above.

The invention relates also to a method for preventing or treating atherosclerosis, comprising the administration of an effective amount of the composition comprising EFD to a patient suffering from or susceptible to atherosclerosis, as defined above.

The present invention will be further illustrated by the additional description and drawings which follow, which refer to examples illustrating the prevention and treatment of atherosclerosis by EFD treatment in three experimental models of atherosclerosis in mice. It should be understood however that these examples are given only by way of illustration of the invention and do not constitute in anyway a limitation thereof.

BRIEF DESCRIPTION OF DRAWINGS

FIG. 1: Long-term EFD BCG treatment modifies serum cytokine levels and induces an immunomodulatory profile in $ApoE^{-/-}$ mice. Cytokines increased in individual serum samples of $ApoE^{-/-}$ mice bimonthly treated 3 times with 100 μg of EFD injected subcutaneously (SC; striped bars) as compared to PBS-treated mice (open bars; n=6 mice per group). Statistical difference with PBS-treated mice is indicated: ***: P≦0.001.

FIG. 2: Long-term EFD BCG treatment modifies serum cytokine levels and induces an immunomodulatory profile in $ApoE^{-/-}$ mice. Cytokines and chemokines reduced in individual serum samples of $ApoE^{-/-}$ mice bimonthly treated 3 times with 100 μg of EFD injected subcutaneously (SC; striped bars) as compared to PBS-treated mice (open bars; n=6 mice per group). Statistical difference with PBS-treated mice is indicated: : P≦0.01*: P≦0.001.

FIG. 3: Cytokines and chemokines remaining unchanged in individual serum samples of ApoE−/− mice bimonthly treated 3 times with 100 μg of EFD injected subcutaneously (SC; striped bars) as compared to PBS-treated mice (open bars; n=6 mice per group).

FIG. 4: EFD BCG affects the activation of key transcription factors associated with inflammation in $ApoE^{-/-}$ mice. NF-κB (open bars) and PPARγ (striped bars) binding to specific DNA motifs in spleen cell nuclear extracts of ApoE−/− mice bimonthly treated 3 times with 100 μg of EFD injected subcutaneously (SC) as compared to PBS-treated mice. n=6 mice per group. Statistical difference with PBS-treated mice is indicated: : P≦0.01*: P≦0.001. EFD BCG has antiinflammatory effects, as evidenced by decreased NFκB translocation and increased PPARγ expression after EFD BCG treatment, compared with PBS.

FIG. 5: Long-term EFD BCG treatment modifies serum cytokine levels and induces an immunomodulatory profile in $ApoE^{-/-}$ mice. Cytokines and chemokines increased in individual serum samples of $ApoE^{-/-}$ mice monthly treated 6 times with 100 μg of EFD injected subcutaneously (striped bars) as compared to PBS-treated mice (open bars; n=6 mice per group). Statistical difference with PBS-treated mice is indicated: ***: P≦0.001.

FIG. 6: Long-term EFD BCG treatment modifies serum cytokine levels and induces an immunomodulatory profile in $ApoE^{-/-}$ mice. Cytokines and chemokines reduced in individual serum samples of $ApoE^{-/-}$ mice monthly treated 6 times with 100 μg of EFD injected subcutaneously (striped bars) as compared to PBS-treated mice (open bars; n=6 mice per group). Statistical difference with PBS-treated mice is indicated: : P≦0.01*: P≦0.001.

FIG. 7 illustrates cytokines remaining unchanged in individual serum samples of $ApoE^{-/-}$ mice monthly treated 6 times with 100 g of EFD injected subcutaneously (striped bars) as compared to PBS-treated mice (open bars; n=6 mice per group).

FIG. 8: EFD BCG affects the activation of key transcription factors associated with inflammation and immunoregulation in ApoE−/− mice. Three pools of 2 splenocyte extracts from mice treated 6 times monthly with PBS or EFD BCG (n=6 mice per group), analyzed by Western blot for RORγt, T-bet, GATA3, and Foxp3. β-actin was used as internal control. EFD BCG initiates immunoregulatory responses by increasing T-bet (Th1 signature) and FOXP3 (Treg signature) and decreasing RORγt and GATA-3, respectively Th17 and Th2 signatures.

Figure 9:
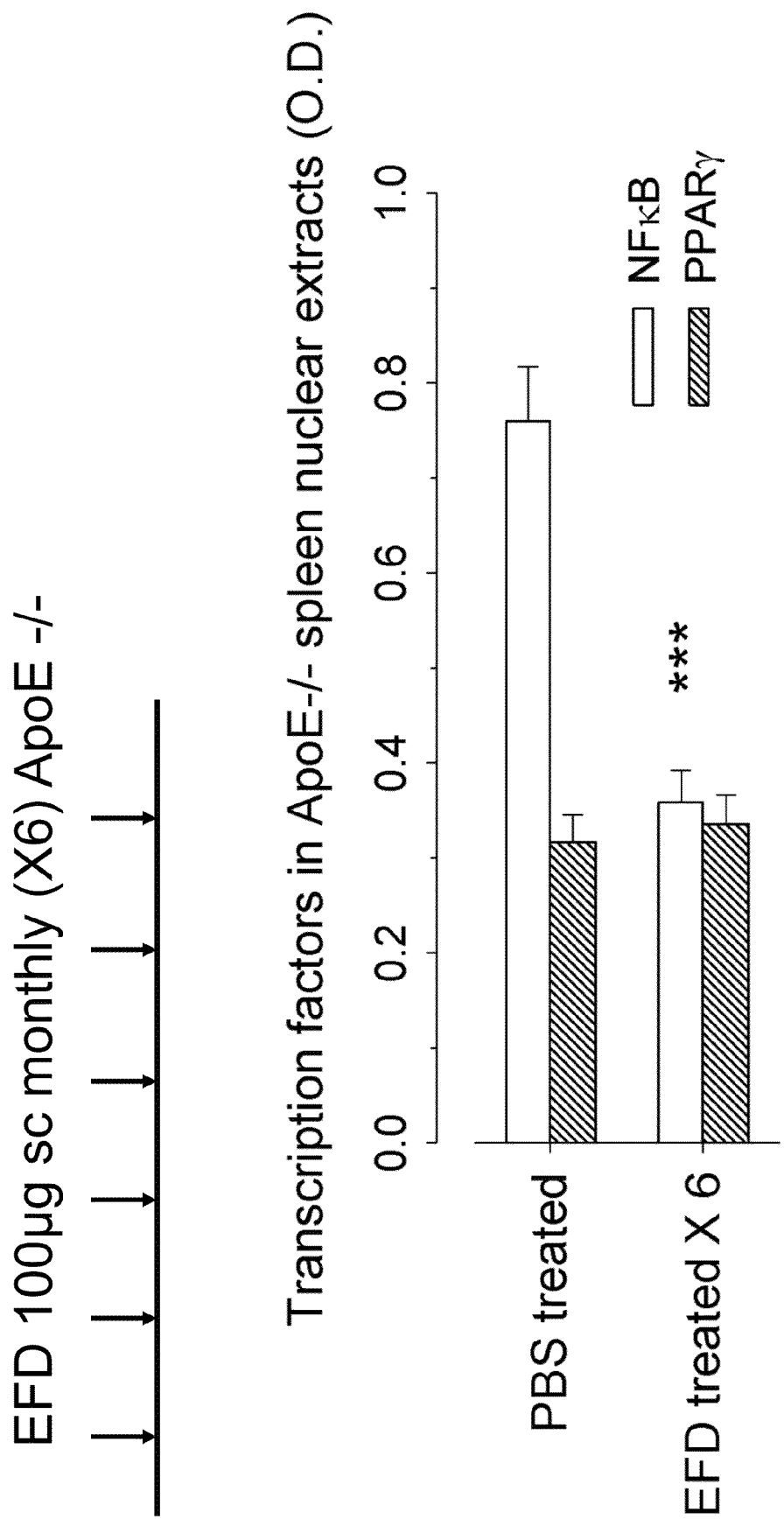

FIG. 9: EFD BCG affects the activation of key transcription factors associated with inflammation in ApoE$^{-/-}$ mice. NF-κB (open bars) and PPARγ (striped bars) binding to specific DNA motifs in spleen cell nuclear extracts of ApoE−/− mice monthly treated 6 times with 100 μg of EFD injected subcutaneously as compared to PBS-treated mice (n=6 mice per group). Statistical difference with PBS-treated mice is indicated: *: P≦0.001. EFD BCG has antiinflammatory effects, as evidenced by decreased NFκB translocation after EFD BCG treatment, compared with PBS. Statistical difference with PBS-treated mice is indicated: *: P≦0.001. EFD BCG has antiinflammatory effects, as evidenced by decreased NFκB translocation after EFD BCG treatment, compared with PBS.

Figure 5:
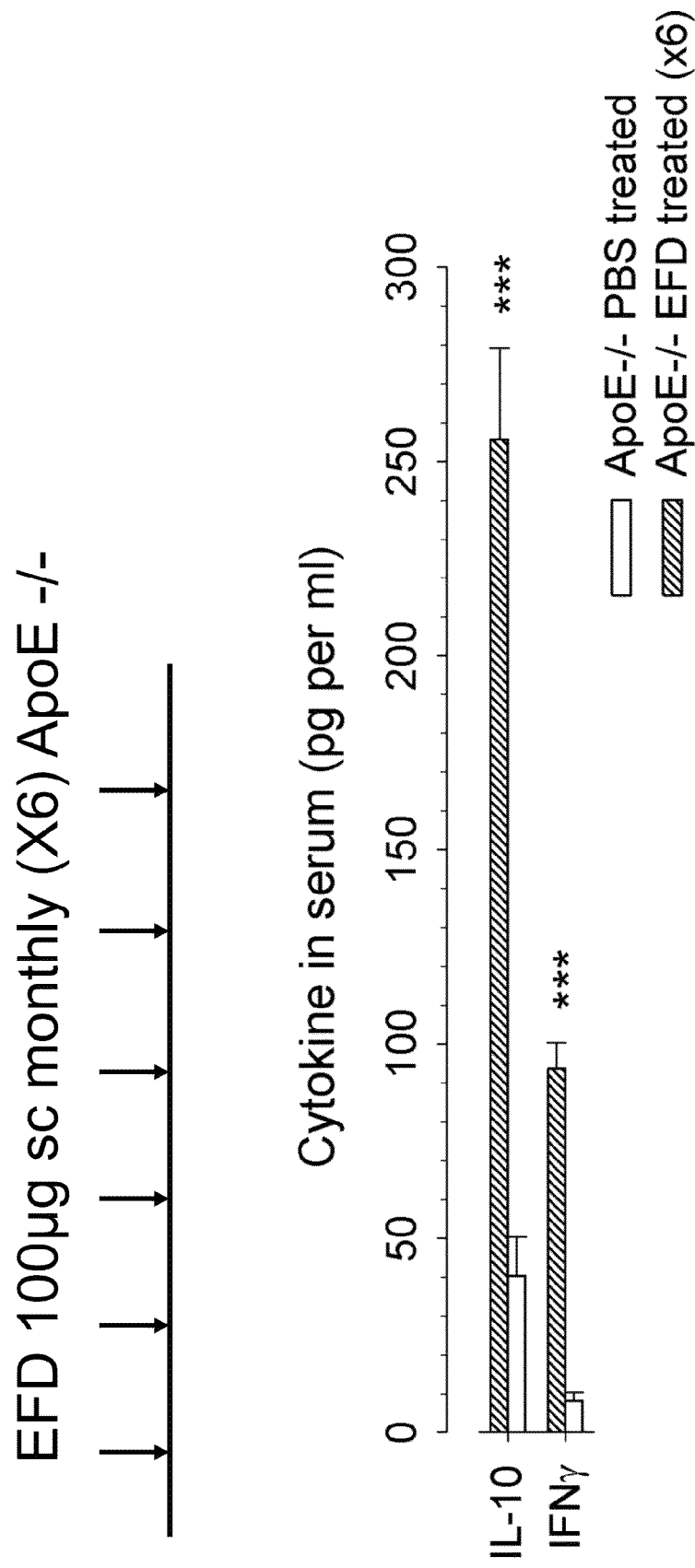
Figure 6:
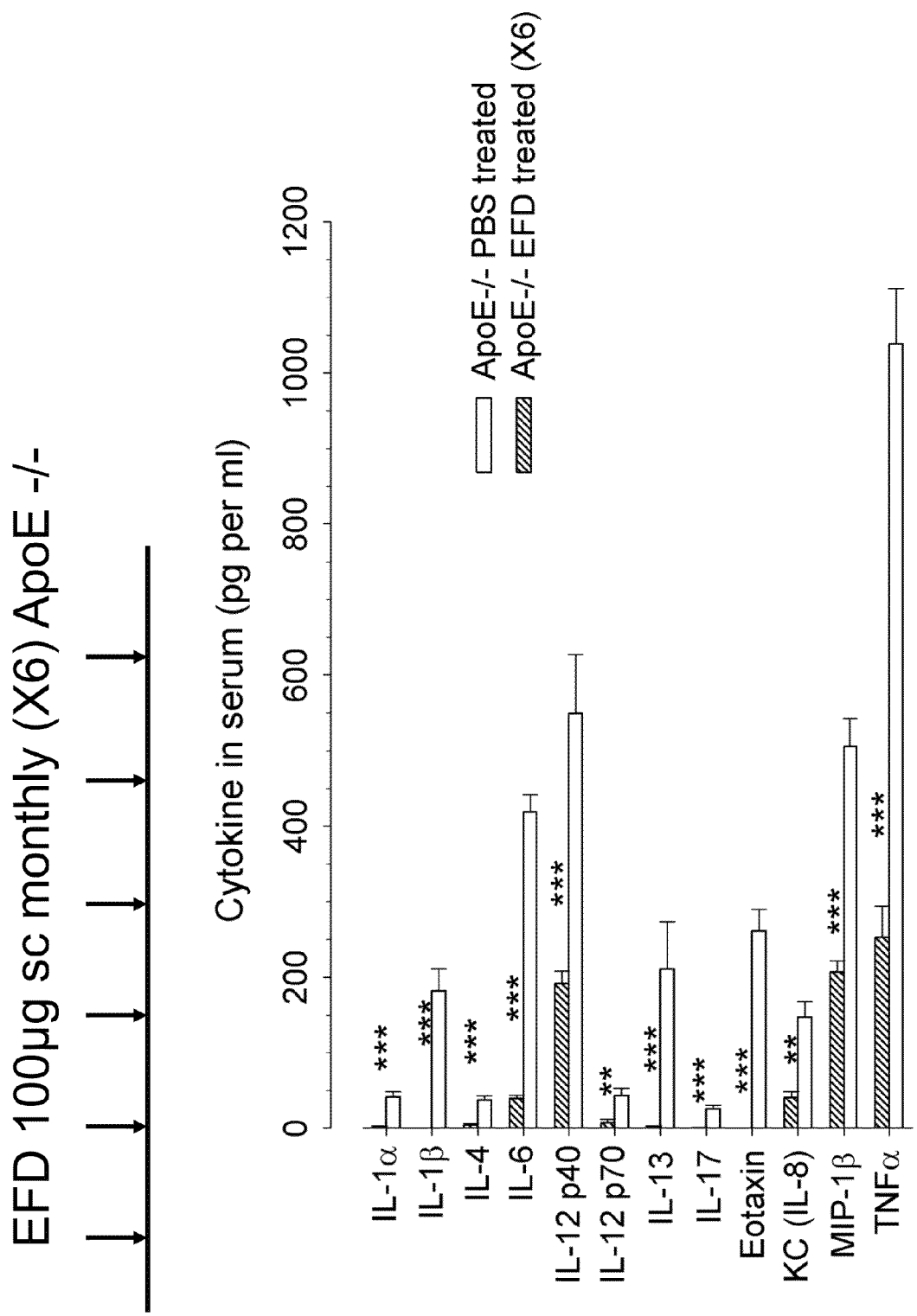
Figure 10:
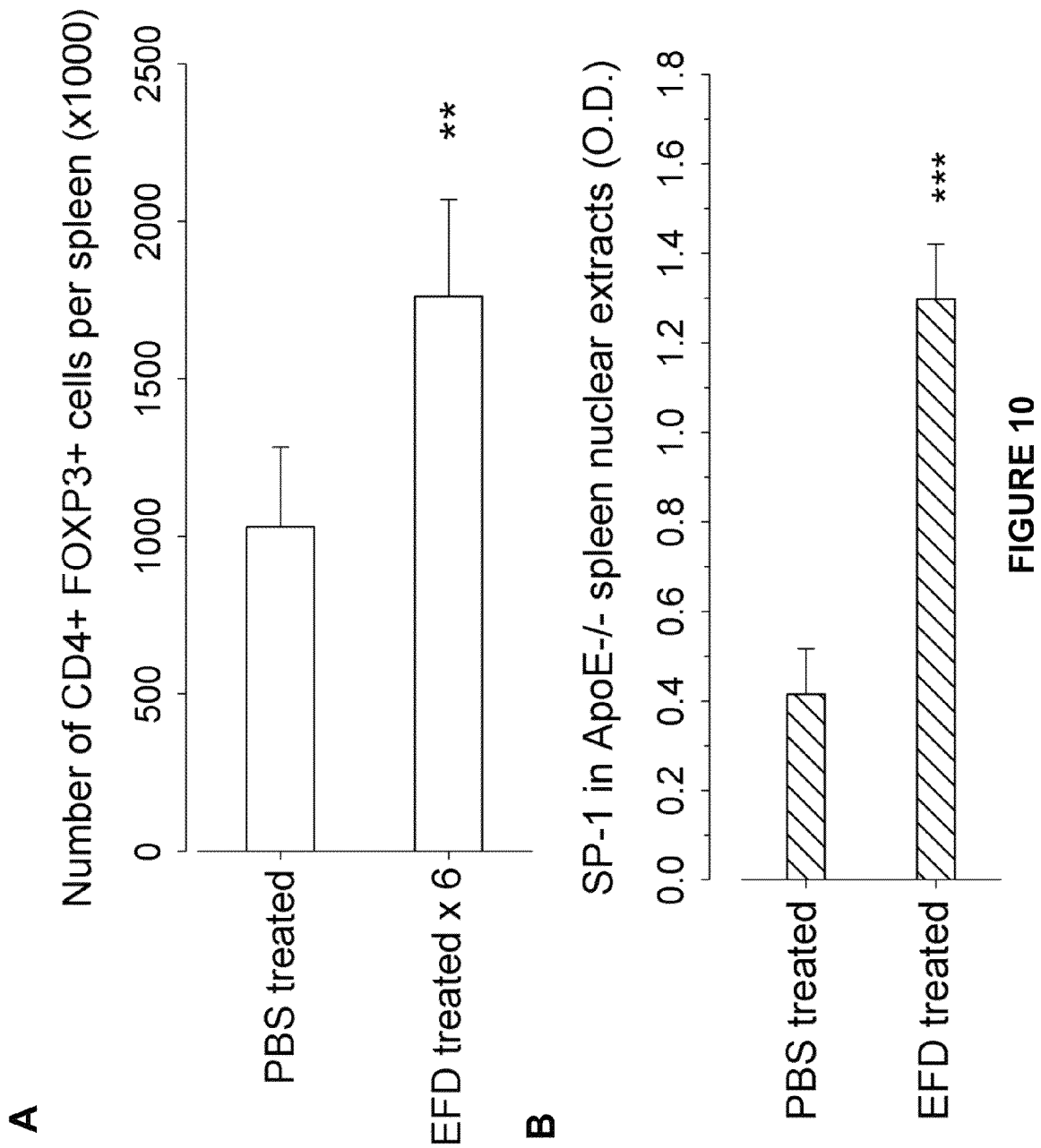

FIG. 10: Long-term EFD BCG treatment induced an immunoregulatory profile in ApoE$^{-/-}$ mice. Mice were injected subcutaneously at age 6, 10, 14, 18, 22, and 26 weeks with 100 μg EFD (n=6) or 100 μl PBS (n=6) and sacrificed at age 30 weeks. (A) Absolute number of CD4$^+$Foxp3$^+$ lymphocytes (analyzed by flow cytometry) in the spleens of PBS- (n=6) or EFD BCG-treated mice (n=6) at week 30. (B) Binding of SP-1 in splenic nuclear extracts of individual PBS- (n=6) or EFD-treated mice (n=6). Statistical difference with PBS-treated mice is indicated: : P≦0.01*: P≦0.001. The higher expression of the SP-1 transcription factor correlates with the higher production of IL-10 found in the sera of EFD treated mice (FIG. 5). These data indicate that EFD BCG initiates immunoregulatory responses by activating SP-1, an important component of IL-10 mediated immunoregulation. EFD-treated mice had a significantly higher number of CD4$^+$ FOXP3$^+$T cells (Treg cells) than PBS treated mice.

Figure 11:
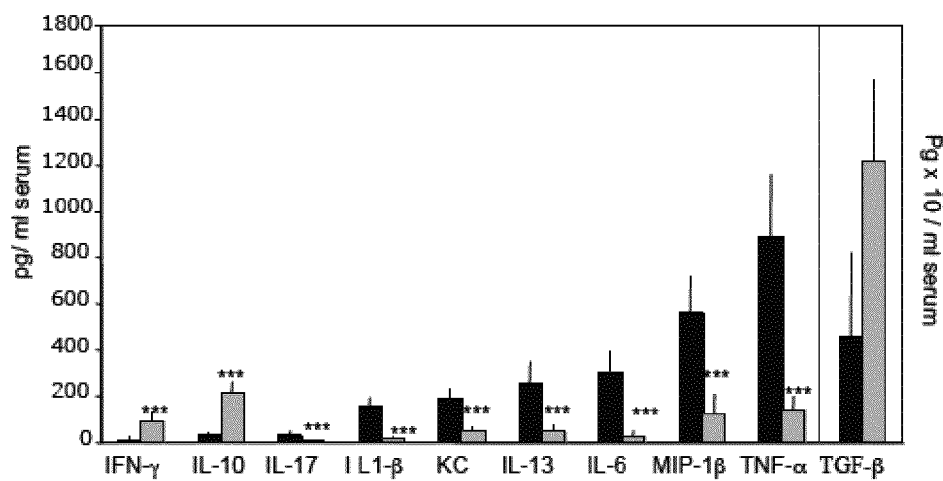

FIG. 11: Long-term EFD BCG treatment modifies serum cytokine levels and induces an immunomodulatory profile in ApoE$^{-/-}$ mice. TGF-β increased in individual serum samples of ApoE−/− mice monthly treated 6 times with 100 μg of EFD BCG injected subcutaneously (grey bar) as compared to PBS treated mice (black bar; n=6 mice per group). ***: P≦0.001.

Figure 12:
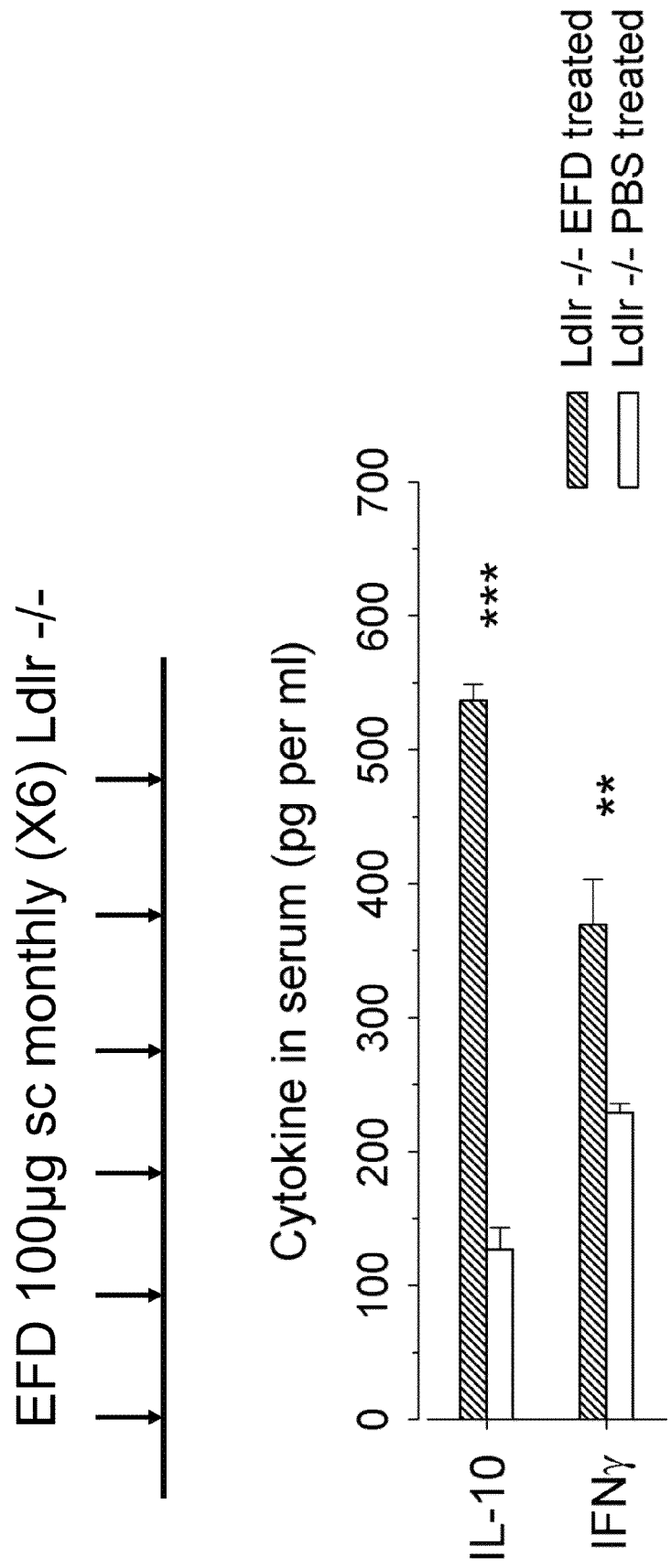

FIG. 12: Long-term EFD BCG treatment modifies serum cytokine levels and induces an immunomodulatory profile in Ldlr−/− mice. Cytokines increased in individual serum samples of Ldlr−/− mice monthly treated 6 times with 100 μg of EFD injected subcutaneously (striped bars) as compared to PBS-treated mice (open bars; n=6 mice per group). Statistical difference with PBS-treated mice is indicated: : P≦0.01*: P≦0.001.

Figure 13:
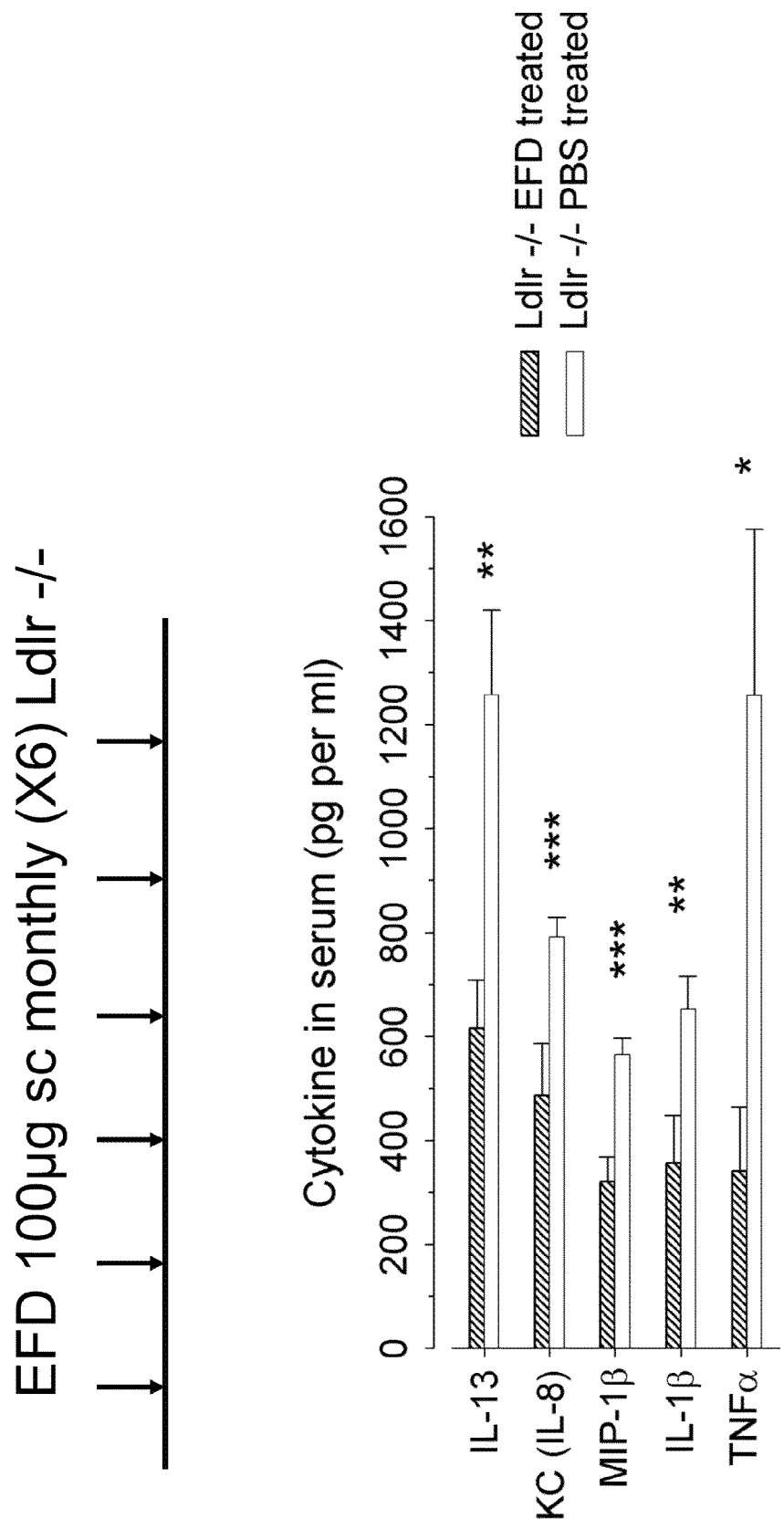

FIG. 13: Long-term EFD BCG treatment modifies serum inflammatory cytokine and chemokine levels in Ldlr−/− mice. Cytokines and chemokines are reduced in individual serum samples of Ldlr−/− mice monthly treated 6 times with 100 μg of EFD injected subcutaneously (striped bars) as compared to PBS-treated mice (open bars; n=6 mice per group). Statistical difference with PBS-treated mice is indicated: *: P≦0.05: P≦0.01*: P≦0.001.

Figure 14:
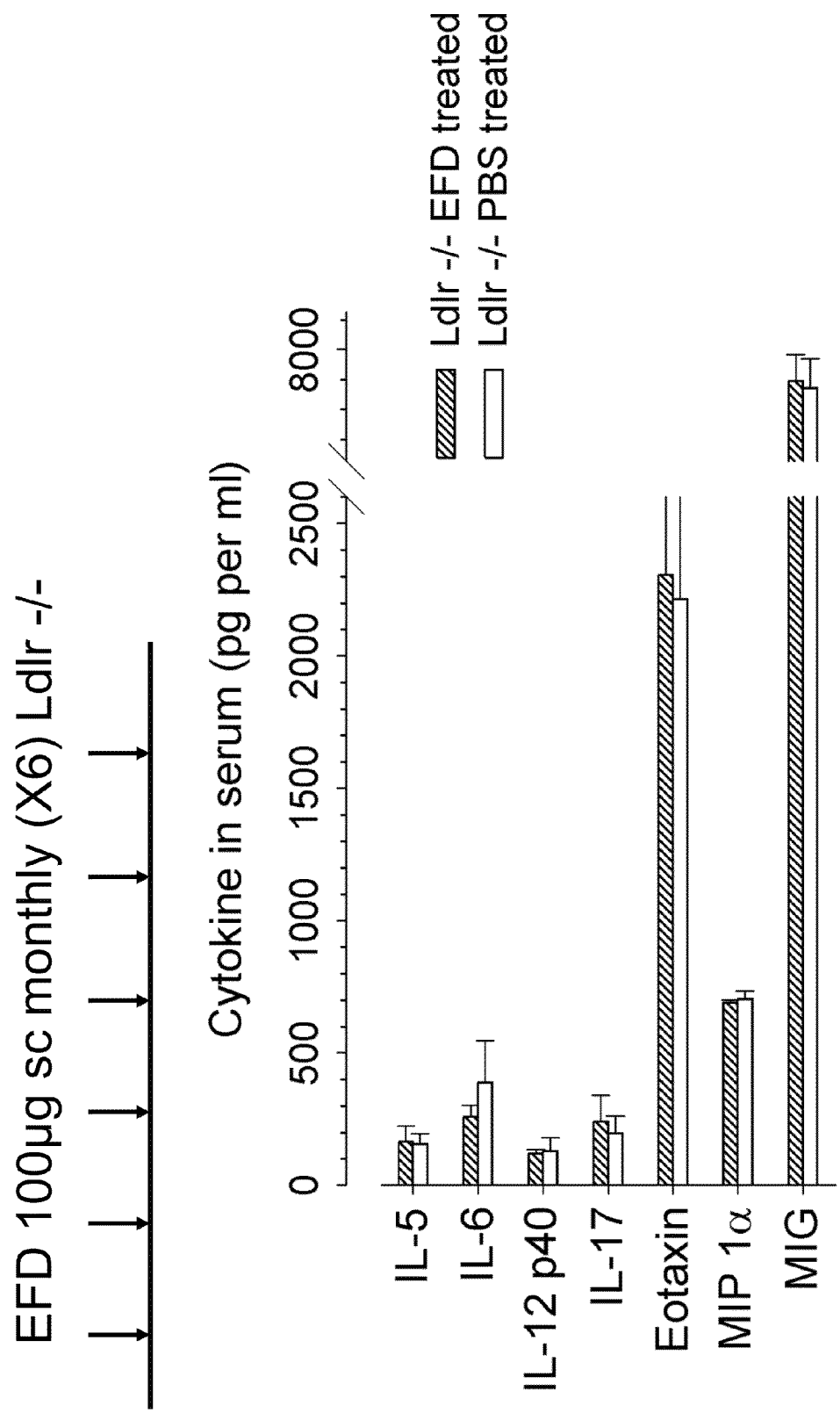

FIG. 14 illustrates the cytokines and chemokines remaining unchanged in individual serum samples of Ldlr−/− mice monthly treated 6 times with 100 μg of EFD injected subcutaneously (striped bars) as compared to PBS-treated mice (open bars; n=6 mice per group).

Figure 15:
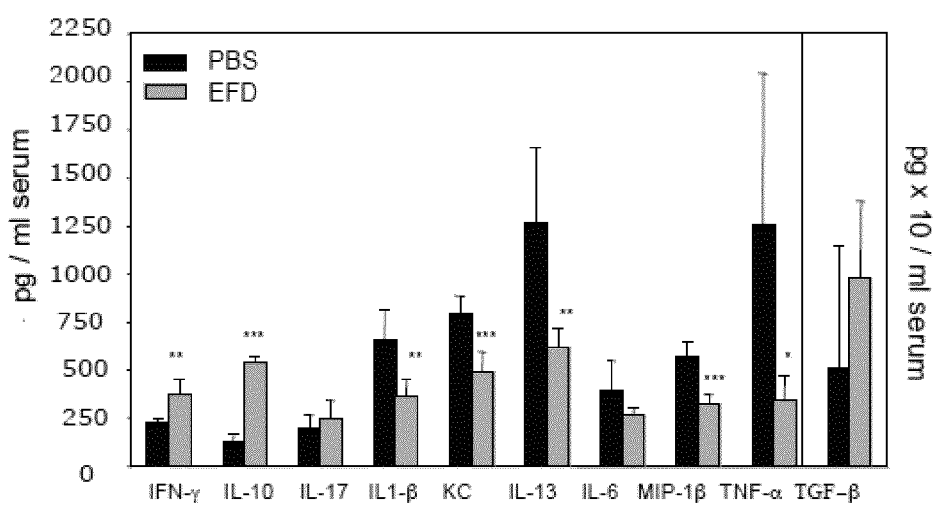

FIG. 15: Long-term EFD BCG treatment modifies serum cytokine levels and induces an immunomodulatory profile in Ldlr−/− mice. TGF-β levels increased weakly in individual serum samples of Ldlr−/− mice monthly treated 6 times with 100 μg of EFD BCG injected subcutaneously (grey bar) as compared to PBS treated mice (black bars; n=6 mice per group).

Figure 16:
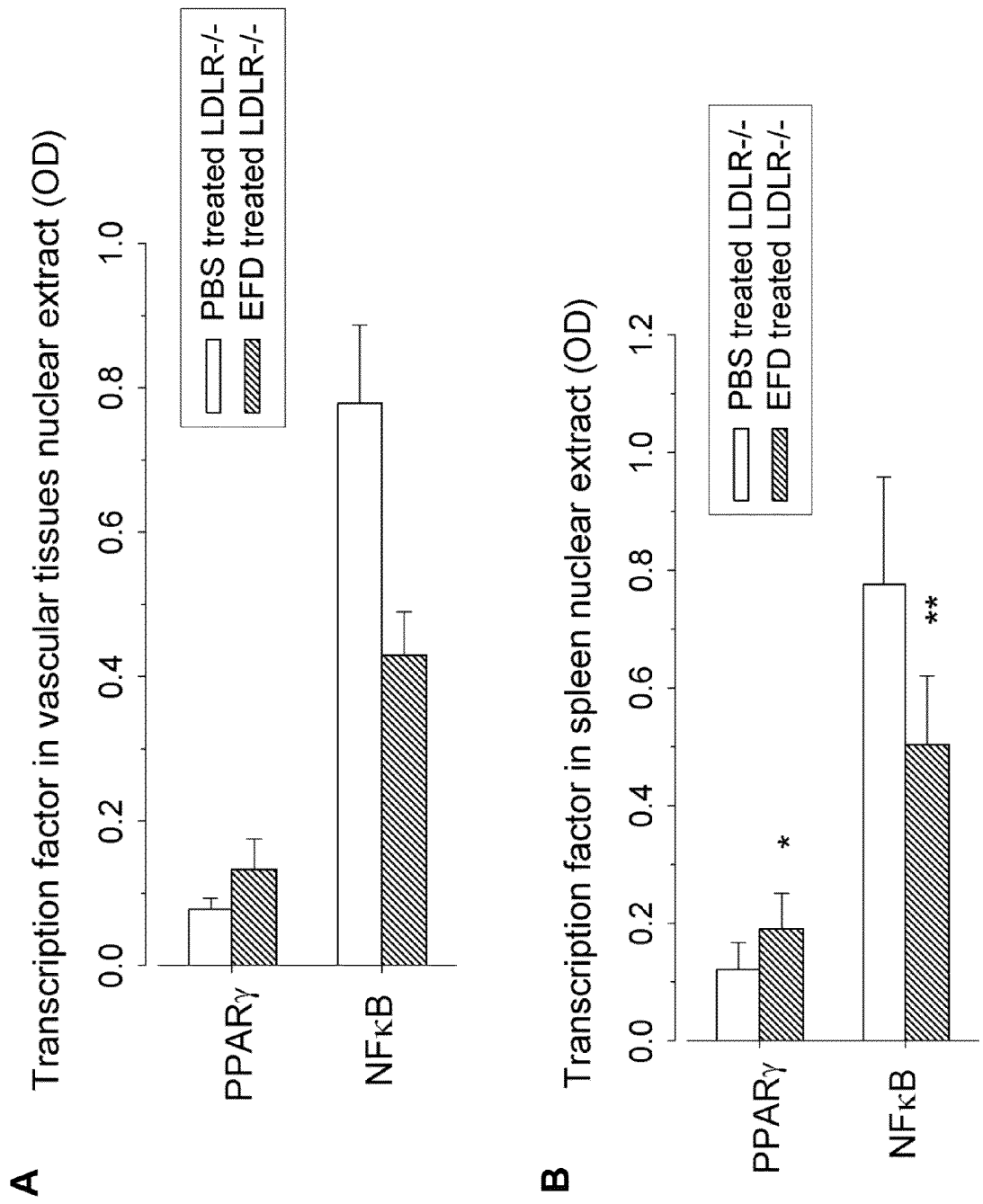

FIG. 16: EFD BCG affects the activation of key transcription factors associated with inflammation in Ldlr−/− mice. NF-κB and PPARγ binding to specific DNA motifs in nuclear extracts of vascular tissues from 2 pools of 3 mice (A) and of individual spleens (B) of mice treated 6 times monthly with PBS (open bars) or EFD BCG (striped bars; n=6 mice per group). EFD BCG has antiinflammatory effects, as evidenced by decreased NFκB translocation and increased PPARγ expression in both organs after EFD BCG treatment, compared with PBS. Statistical difference with PBS-treated mice is indicated in (B): *: P≦0.05**: P≦0.01. As 2 pools of 3 samples were shown in (A), no statistical analysis was performed.

Figure 17:
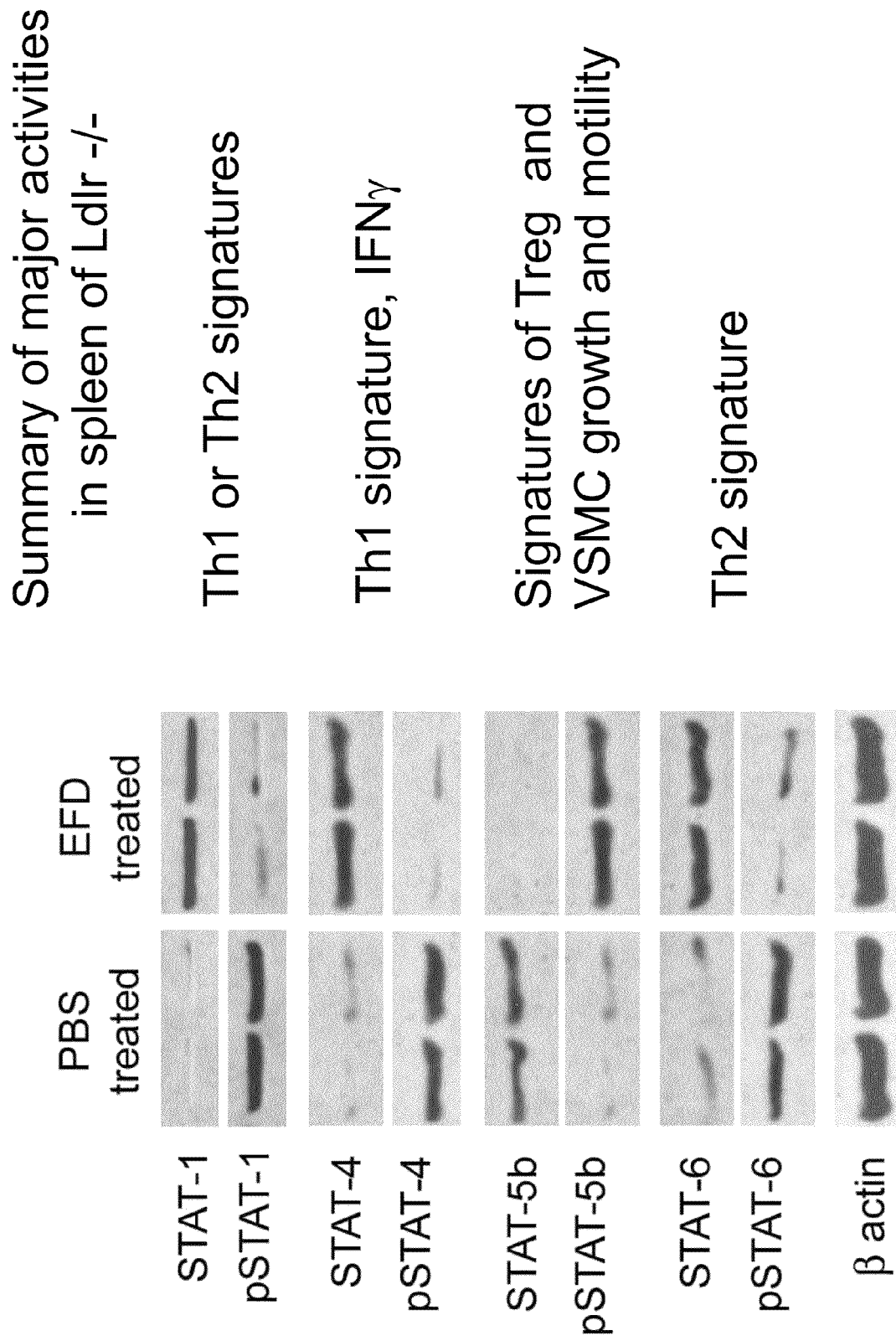

FIG. 17: EFD BCG affects the activation of key transcription factors associated with inflammation and immunoregulation in Ldlr−/− mice. Two pools of 3 splenocyte extracts from mice treated 6 times monthly with PBS or EFD BCG (n=6 mice per group), analyzed by Western blot for nonphosphorylated and phosphorylated STAT-1, STAT-4, STAT-5b, and STAT-6. β-actin was used as internal control. The phosphorylation of the STATs reflected their activation. EFD BCG has antiinflammatory effects, as evidenced by decreased phosphorylation of STAT-1, STAT-4, and STAT-6. EFD BCG initiates immunoregulatory responses as evidenced by p-STAT-5b activation.

Figure 18:
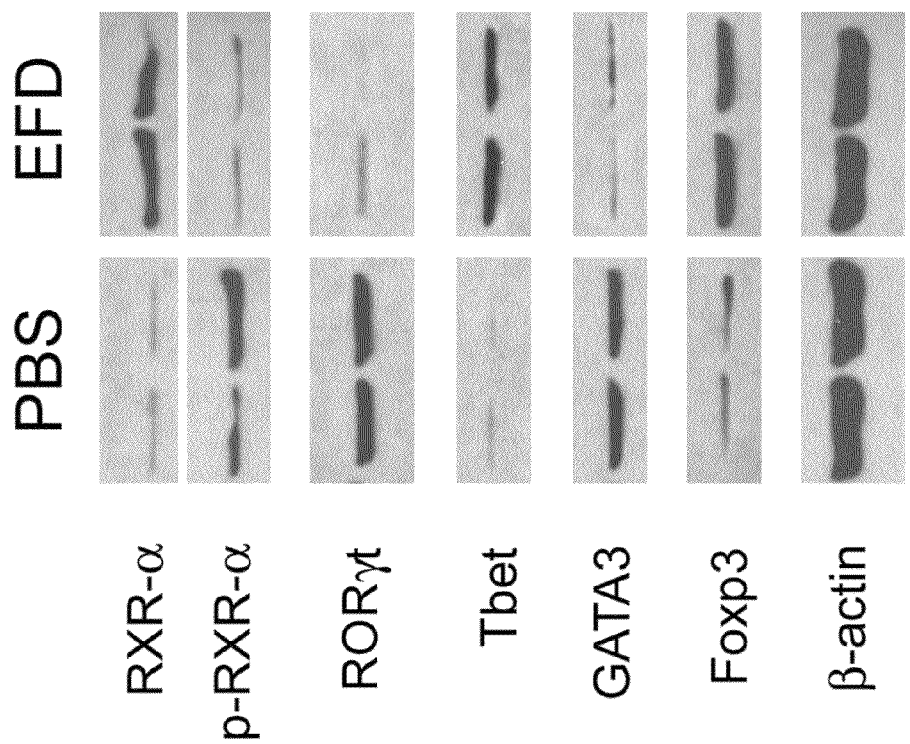

FIG. 18: EFD BCG affects the activation of key transcription factors associated with inflammation and immunoregulation in Ldlr−/− mice. Two pools of 3 splenocyte extracts from mice treated 6 times monthly with PBS or EFD BCG (n=6 mice per group), analyzed by Western blot for nonphosphorylated and phosphorylated RXR-α; RORγt, T-bet, GATA3, and Foxp3. β-actin was used as internal control. EFD BCG initiates immunoregulatory responses by increasing T-bet (Th1 signature) and FOXP3 (Treg signature) and decreasing RORγt and GATA-3, respectively Th17 and Th2 signatures. EFD BCG has also antiinflammatory effects, as evidenced by decreased phosphorylation of RXR-α.

Figure 19:
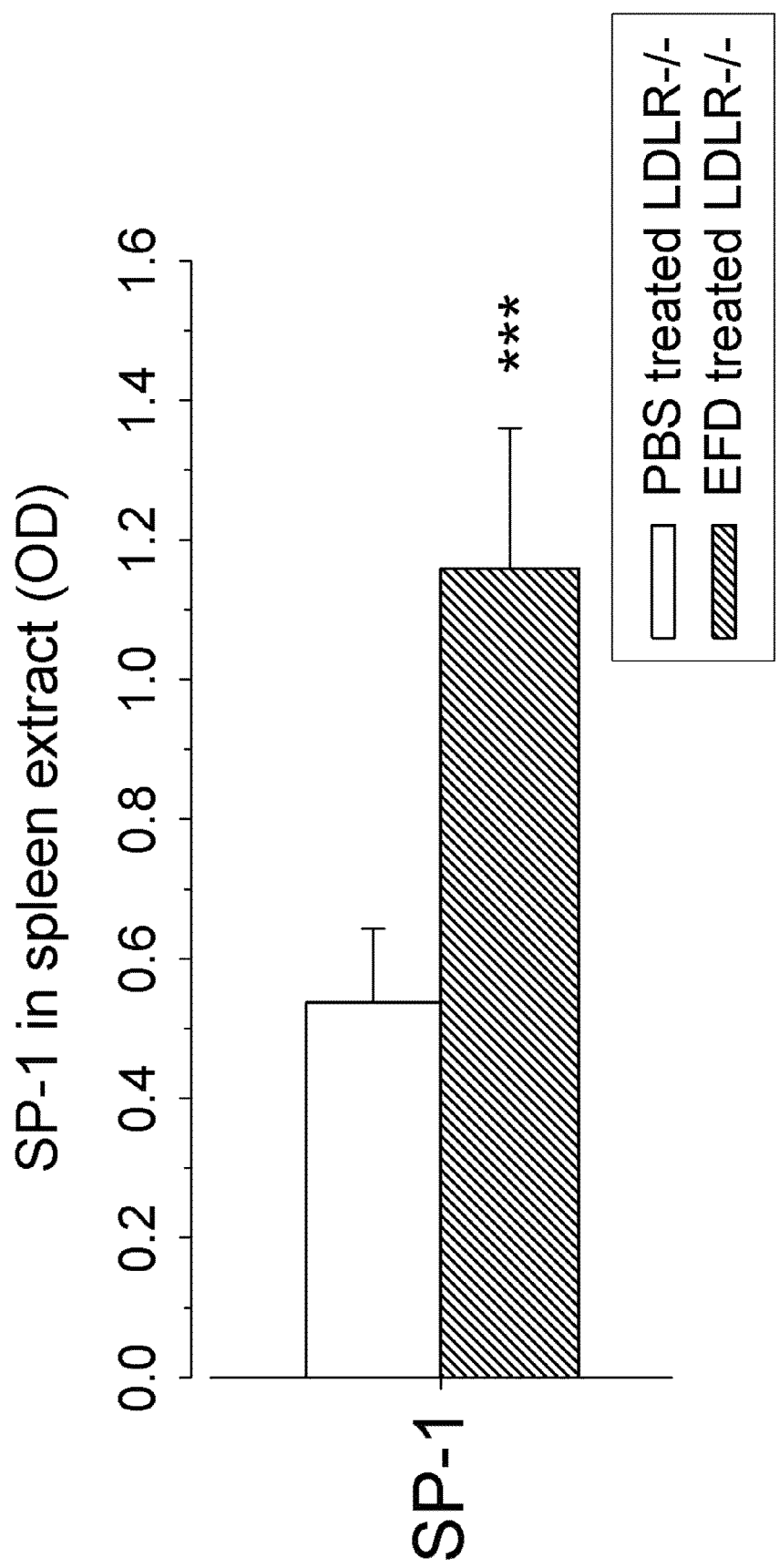

FIG. 19: EFD BCG affects the activation of key transcription factors associated with immunoregulation in Ldlr−/− mice. The binding of SP-1 to its specific DNA motif in individual splenic nuclear extracts from mice treated 6 times monthly with PBS (open bars) or EFD BCG (striped bars; n=6 mice per group). SP-1, an important component of IL-10 mediated immunoregulation is very significantly enhanced after EFD treatment. These data indicate that EFD BCG initiates immunoregulatory responses by activating SP-1. Statistical difference with PBS-treated mice is indicated: ***: P≦0.001.

Figure 20:
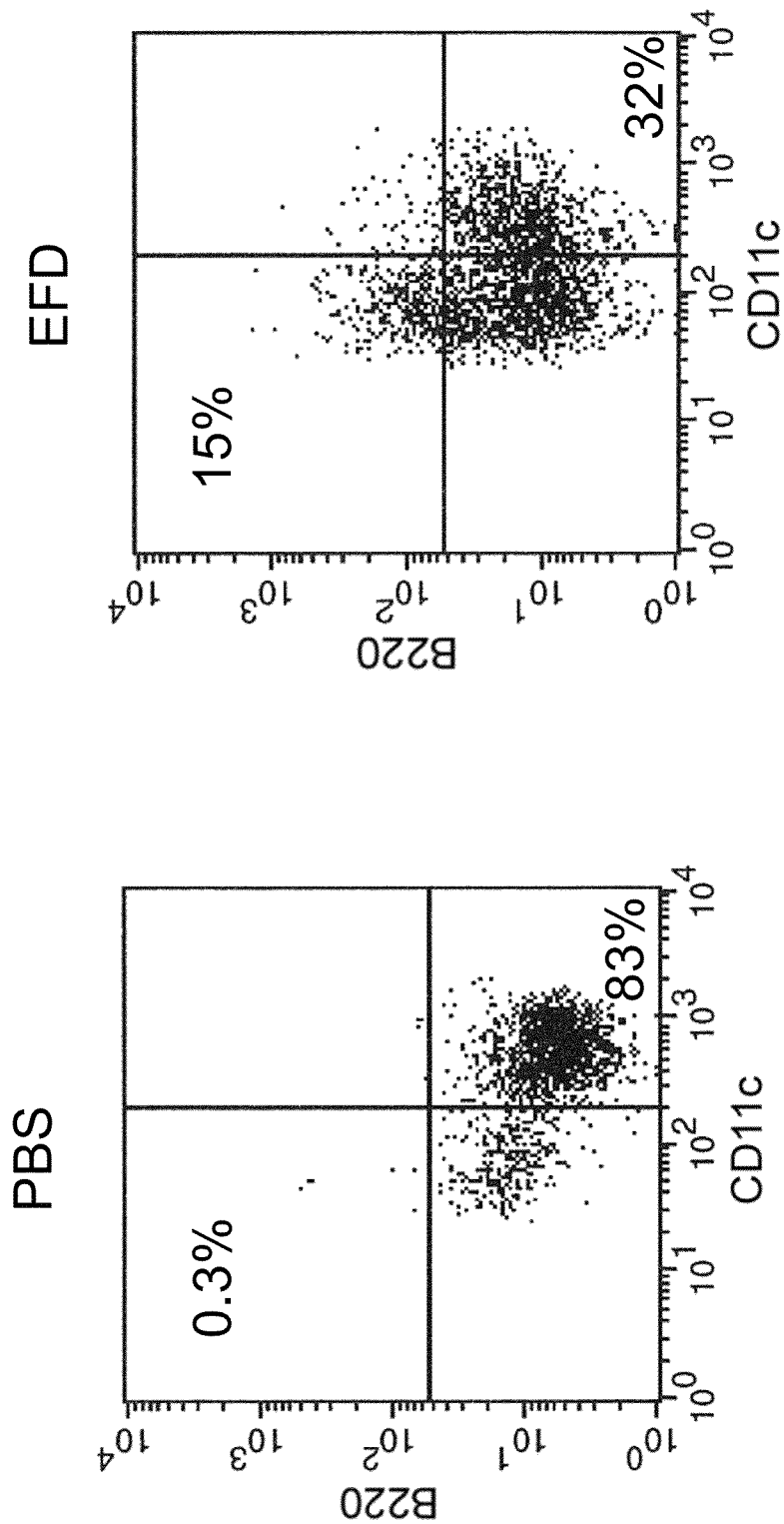

FIG. 20: EFD treatment induced the recruitment of plasmacytoid dendritic cells (pDCs). Flow cytometric analysis of cells recruited to the inguinal draining lymph nodes (DLNs) of Ldlr$^{-/-}$ mice 4 days after the first injection of PBS or EFD BCG (100 μg); within CD11c$^+$ population, CD11c$^{hi}$B220$^{neg}$ cDCs (lower right subdivision) and CD11c$^{low}$/B220$^{hi}$ pDCs (higher left subdivision). Four days after the first subcutaneous injection of EFD, more pDCs (CD11c$^{low}$B220$^{high}$) were detected in EFD BCG mice compared with PBS-injected mice (15% versus 0.3% of gated CD11c+ cells). By contrast, fewer conventional DCs (cDCs; CD11c$^{high}$B220$^{neg}$) were observed in the DLNs after EFD BCG injection compared with PBS (32% versus 83% of gated CD11c+ cells).

Figure 21:
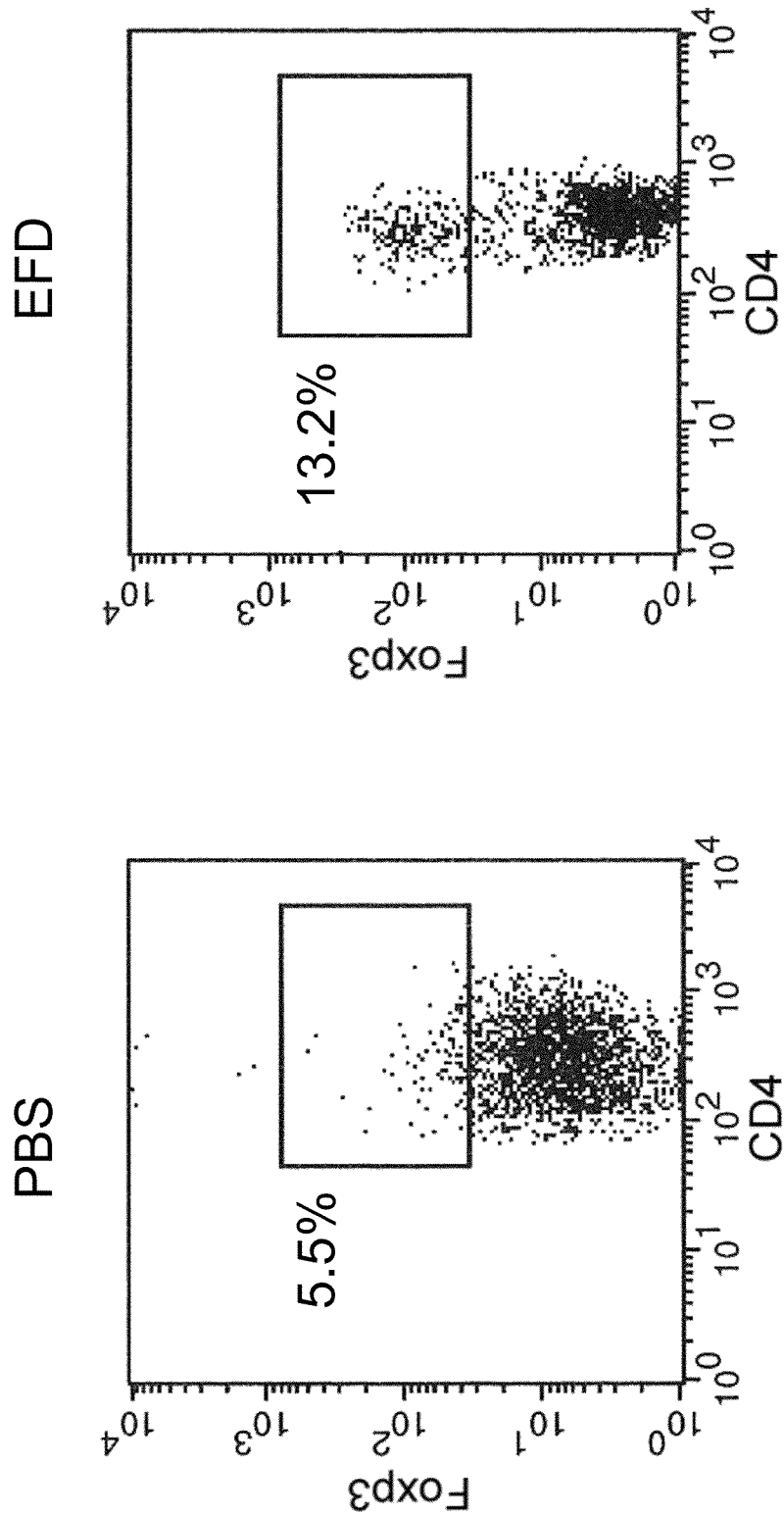

FIG. 21: Plasmacytoid dendritic cells (pDCs) promoted regulatory T cells (Tregs). Flow cytometric analysis of cells recruited to the inguinal draining lymph nodes (DLNs) of Ldlr$^{-/-}$ mice 4 days after the first injection of PBS or EFD BCG (100 μg); within CD4$^+$ population, CD4$^+$Foxp3$^+$Tregs. Four days after the first subcutaneous injection of EFD, the percentage of CD4$^+$Foxp3$^+$Tregs in the DLNs of EFD BCG treated mice rose compared with control mice (13.2% versus 5.5% of gated CD4$^+$ cells).

Figure 22:
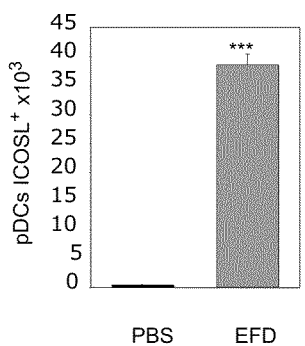
Figure 22:
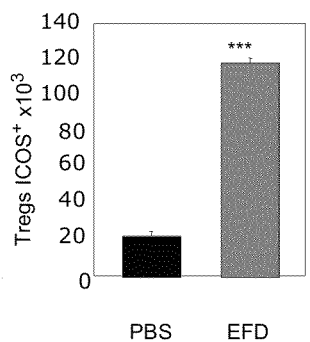

FIG. 22: Long-term EFD BCG treatment induced an immunoregulatory profile in Ldlr−/− mice. Flow cytometric analysis of cells recruited to the inguinal DLNs 4 days after the first injection of PBS or EFD BCG. (A) Number of pDCs expressing ICOS-L in both inguinal DLNs. (B) Number of CD4$^+$CD25$^+$ Tregs expressing ICOS in both inguinal DLNs. * P<0.05,  P<0.01, * P<0.001.

Figure 23:
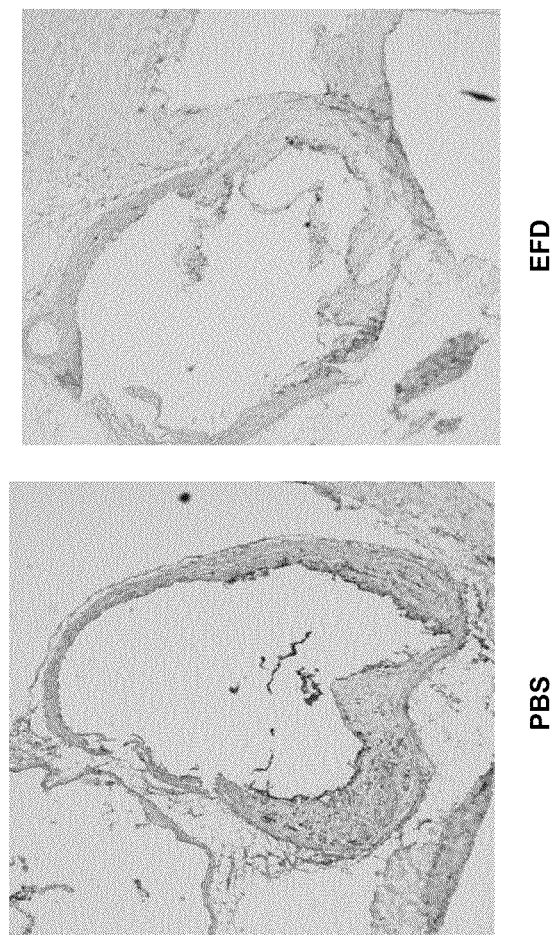
Figure 23:
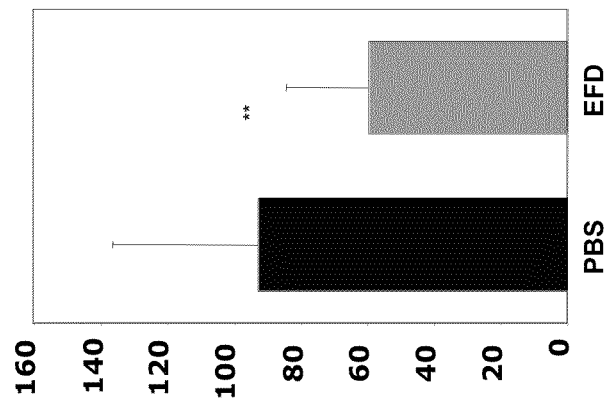

FIG. 23: Long-term EFD BCG treatment reduces lesion size and inflammation in ApoE−/− mice. Mice were injected subcutaneously at age 6, 10, 14, 18, 22, and 26 weeks with 100 μg EFD (n=6) or 100 μl PBS (n=6) and sacrificed at age 30 weeks. (A), Mean cross-sectional area of atherosclerosis lesions in the aortic root (μm$^2$×1000). (B), Representative photomicrographs of macrophage staining (MOMA-2$^+$cells) in the aortic sinuses of mice treated with PBS and EFD BCG. After EFD BCG treatment, mean cross-sectional area of atherosclerotic lesions in the aortic root was significantly lower compared with the control, as was macrophage accumulation.

Figure 24:
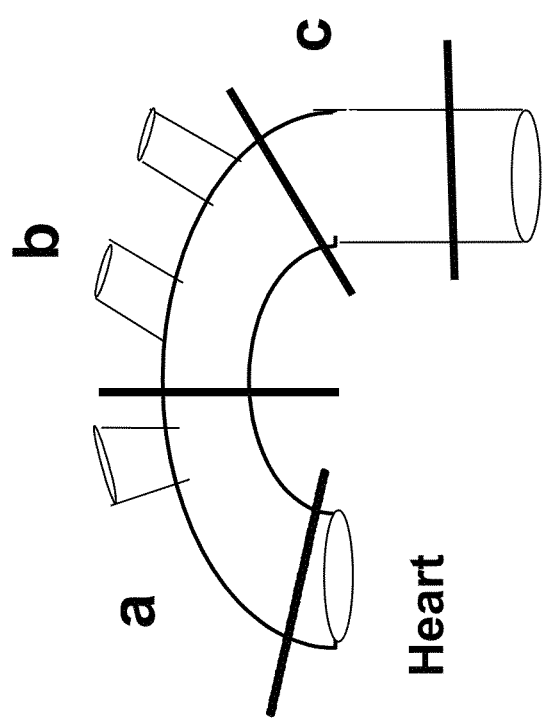

FIG. 24 represents the aortic arch of mice EFD-treated and PBS-treated mice and the different sites (a, b, c) where the area of the atheroma plaques was semi-quantified on hematoxylin-eosin slides.

Figure 25:
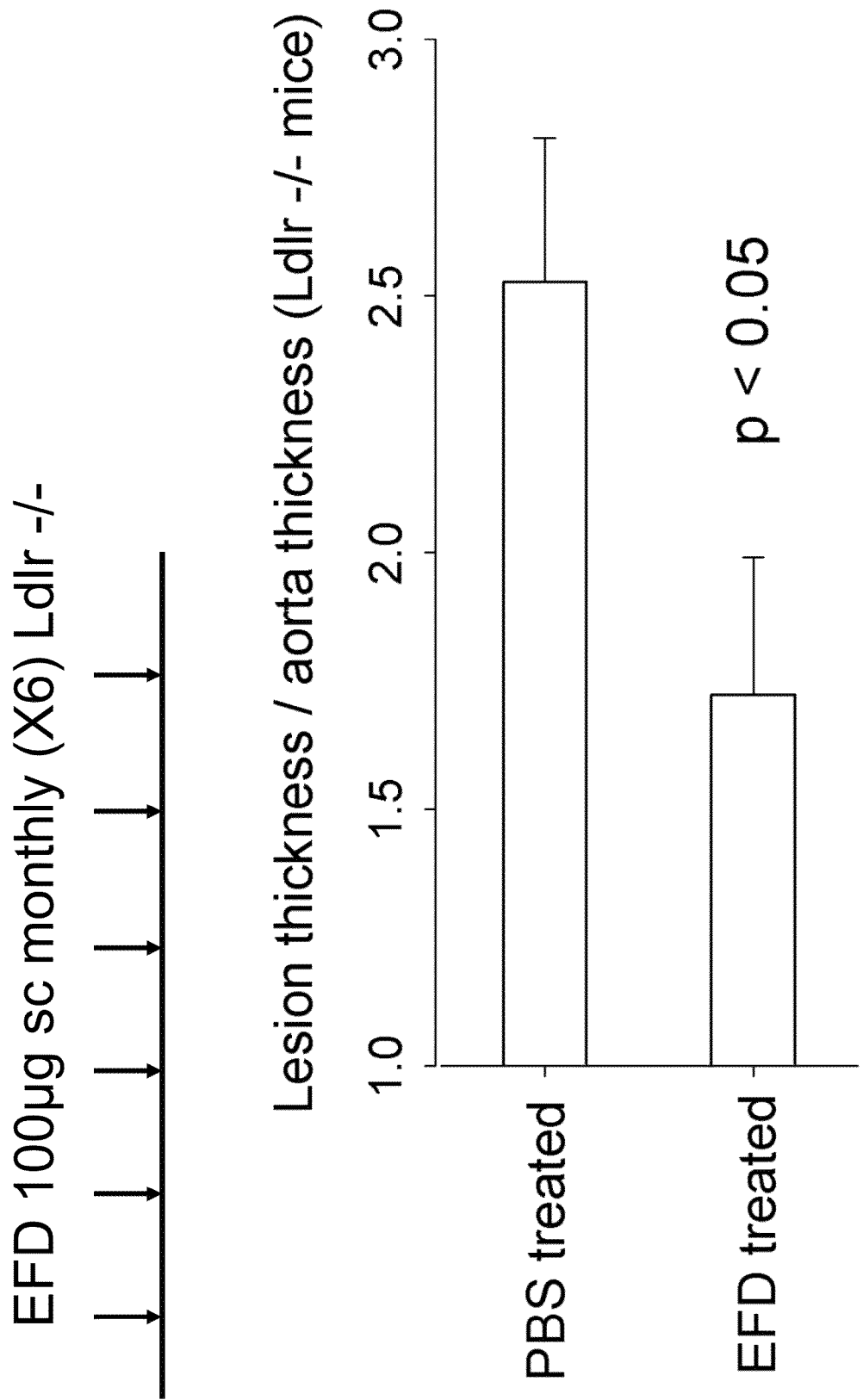

FIG. 25: Long-term EFD BCG treatment reduces atherosclerotic lesions in Ldlr−/− mice. Ldlr−/− mice fed with atherosclerotic diet received (subcutaneously) 100 μl of PBS or 100 μg of EFD at 6, 10, 14, 18, 22 and 26 week-old. Mice were killed at 30 week-old and the mean lesion thickness and aortic thickness were calculated from eight to sixteen aorta arch sections of each mouse. Lesion thickness was analyzed using Leica QWin image analysis software. Results are expressed as the ratio lesion thickness/aorta thickness.

Figure 26:
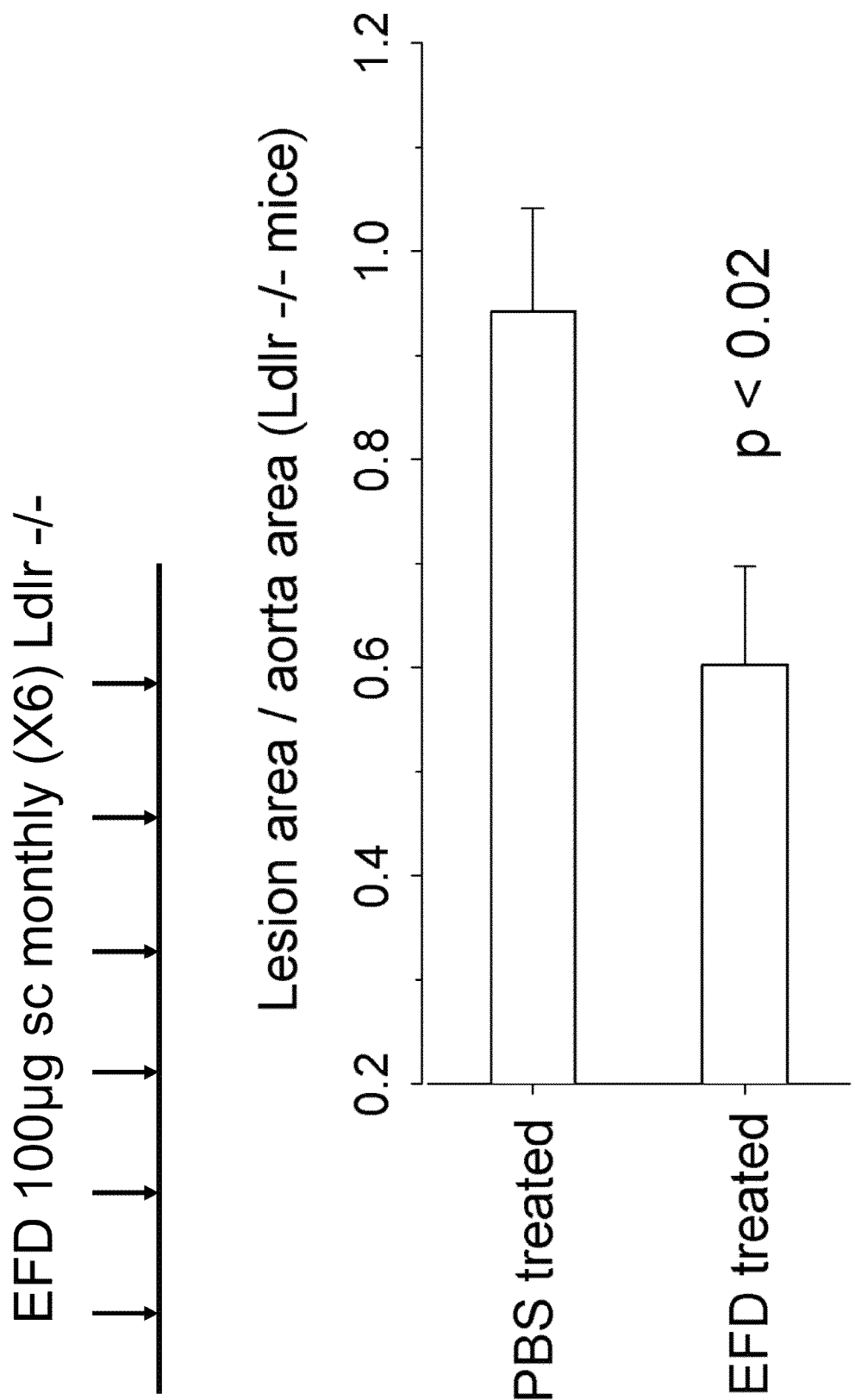

FIG. 26: Long-term EFD BCG treatment reduces atherosclerotic lesions in Ldlr−/− mice. Ldlr−/− mice fed with atherosclerotic diet received (subcutaneously) 100 μl of PBS or 100 μg of EFD at 6, 10, 14, 18, 22 and 26 week-old. Mice were killed at 30 week-old and the mean lesion area and total aortic area were calculated from eight to sixteen aorta arch sections of each mouse. Lesion area was analyzed using Leica QWin image analysis software. Results are expressed as the ratio lesion area/aorta area.

Figure 27:
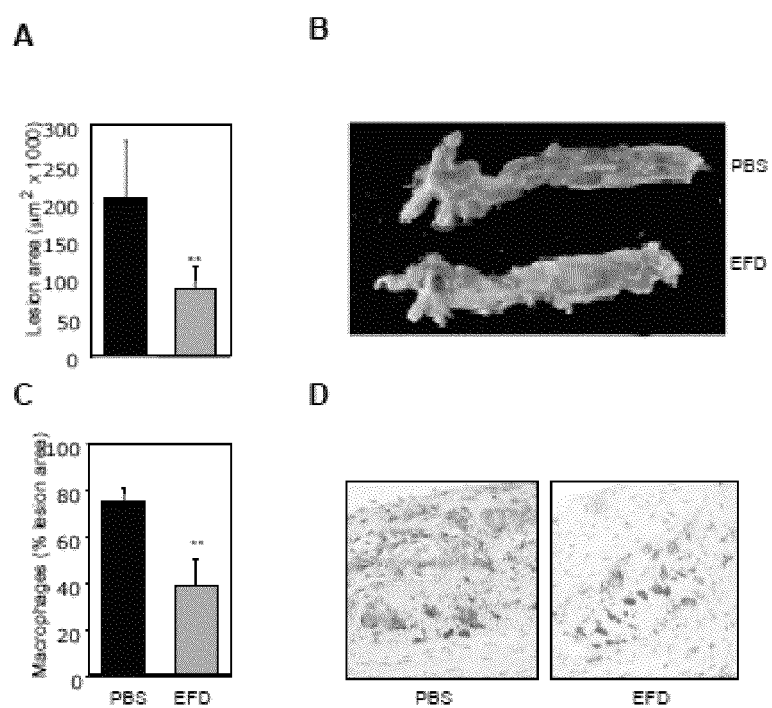

FIG. 27: Long-term EFD BCG treatment reduces atherosclerotic lesions in Ldlr−/− mice. Ldlr−/− mice fed with atherosclerotic diet were injected subcutaneously at age 6, 10, 14, 18, 22 and 26 weeks with 100 μg EFD BCG (n=6) or 100 μl PBS (n=6) and were sacrificed at age 30 weeks. (A), Mean cross-sectional area of the atherosclerosis lesions in the aortic root (μm$^2$×1000). (B), Representative photomicrograph of aortas stained with Sudan IV. (C), Macrophage staining (MOMA-2$^+$cells), expressed as a percentage of stained area to lesional cross-sectional area. (D), Representative micrographs of aortic MOMA-2$^+$ cells in aortic lesions after PBS or EFD BCG treatment. Original magnification×400. ** P<0.01.

Figure 28:
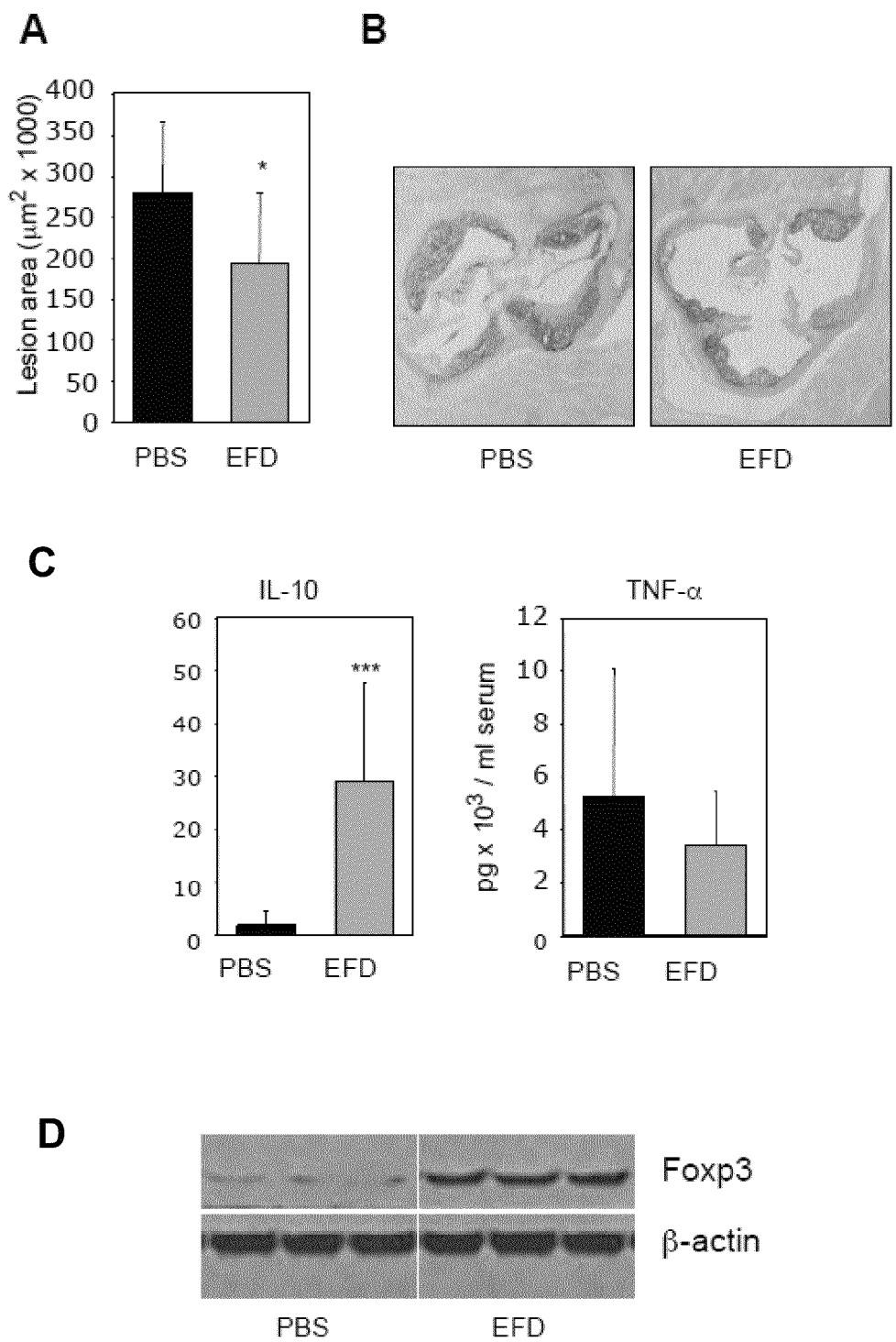

FIG. 28: EFD BCG treatment reduces lesion size and induces an immunoregulatory response in Apoe−/−× CD4dnTβRII mice. Mice were injected subcutaneously at age 6 and 9 weeks with 100 μg EFD BCG (n=9) or 100 μl PBS (n=8), and aortas, spleens, and serum were collected at 12 weeks. (A), Mean cross-sectional area of atherosclerosis lesions in the aortic root (μm$^2$×1000). (B), representative photomicrograph of aortic sinuses after Oil Red 0 staining. (C), Measurements of IL-10 and TNF-α in individual serum by Bio-Plex. (D), Detection of Foxp3 by Western blot in splenocyte extracts. Each band represents pooled splenocyte extracts from 3 mice. * P<0.05, *** P<0.001.

Figure 29:
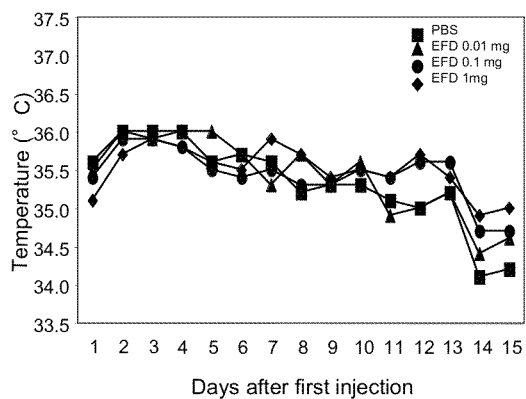
Figure 29:
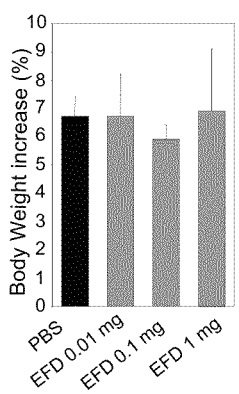
Figure 29:
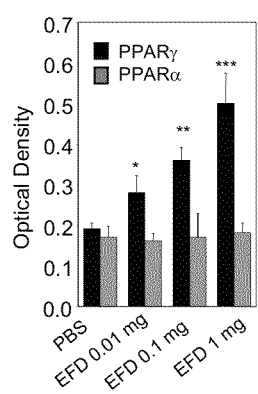

FIG. 29: Increasing doses of EFD BCG do not induce side effects in OF1 outbred Swiss mice. Various doses of EFD (0.01, 0.1, and 1 mg) and 100 μl PBS were administered to OF1 mice subcutaneously daily for 14 days (n=6 per group). (A), Rectal temperature was monitored 24 hours after each injection. (B), Weight of mice each day. (C), PPARγ and PPARα binding to their specific DNA motifs in splenic nuclear extracts at the end of the experiment (Day 15), * P<0.05,  P<0.01, * P<0.001.

Figure 30:
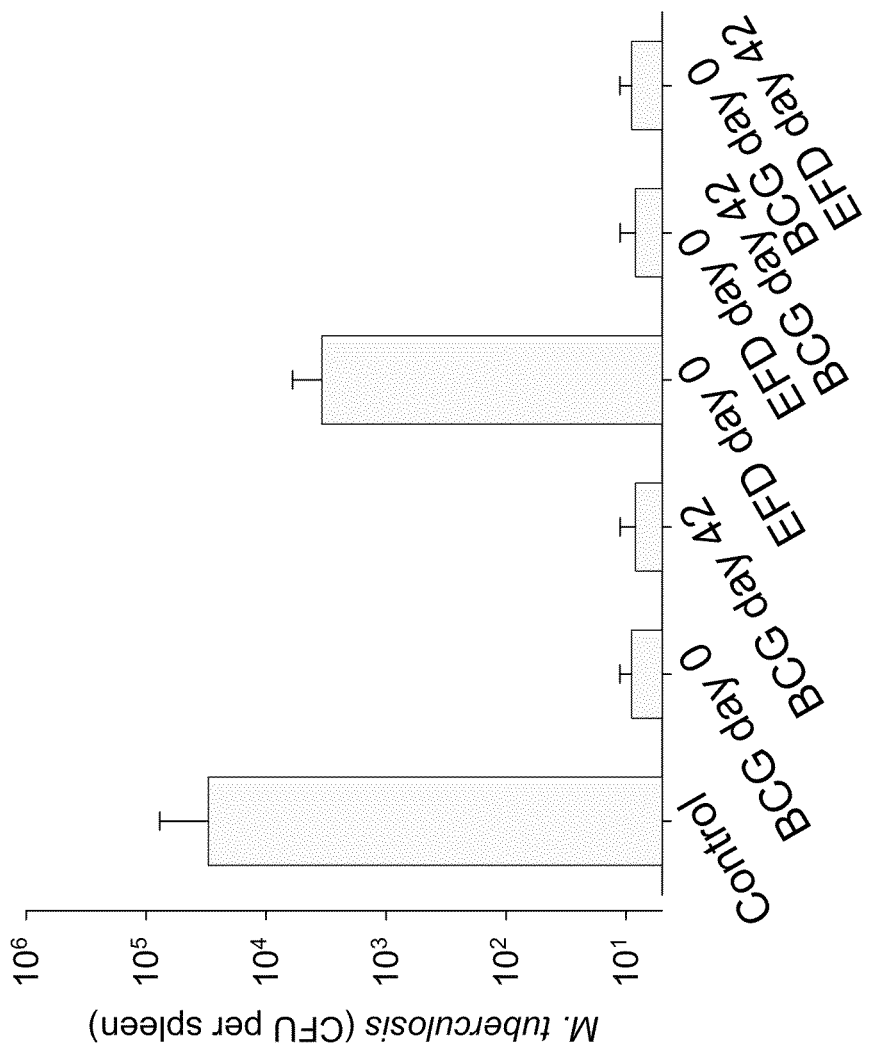

FIG. 30: EFD treatment does not interfere with M. tuberculosis infection or BCG vaccination. Guinea-pigs were treated with EFD before or after BCG injection or without BCG injection. Then, the guinea-pigs were infected with M. tuberculosis and the Colony Forming Units (CFUs) of virulent bacteria in the spleens were counted. n=6 guinea pigs per group.

Figure 31:
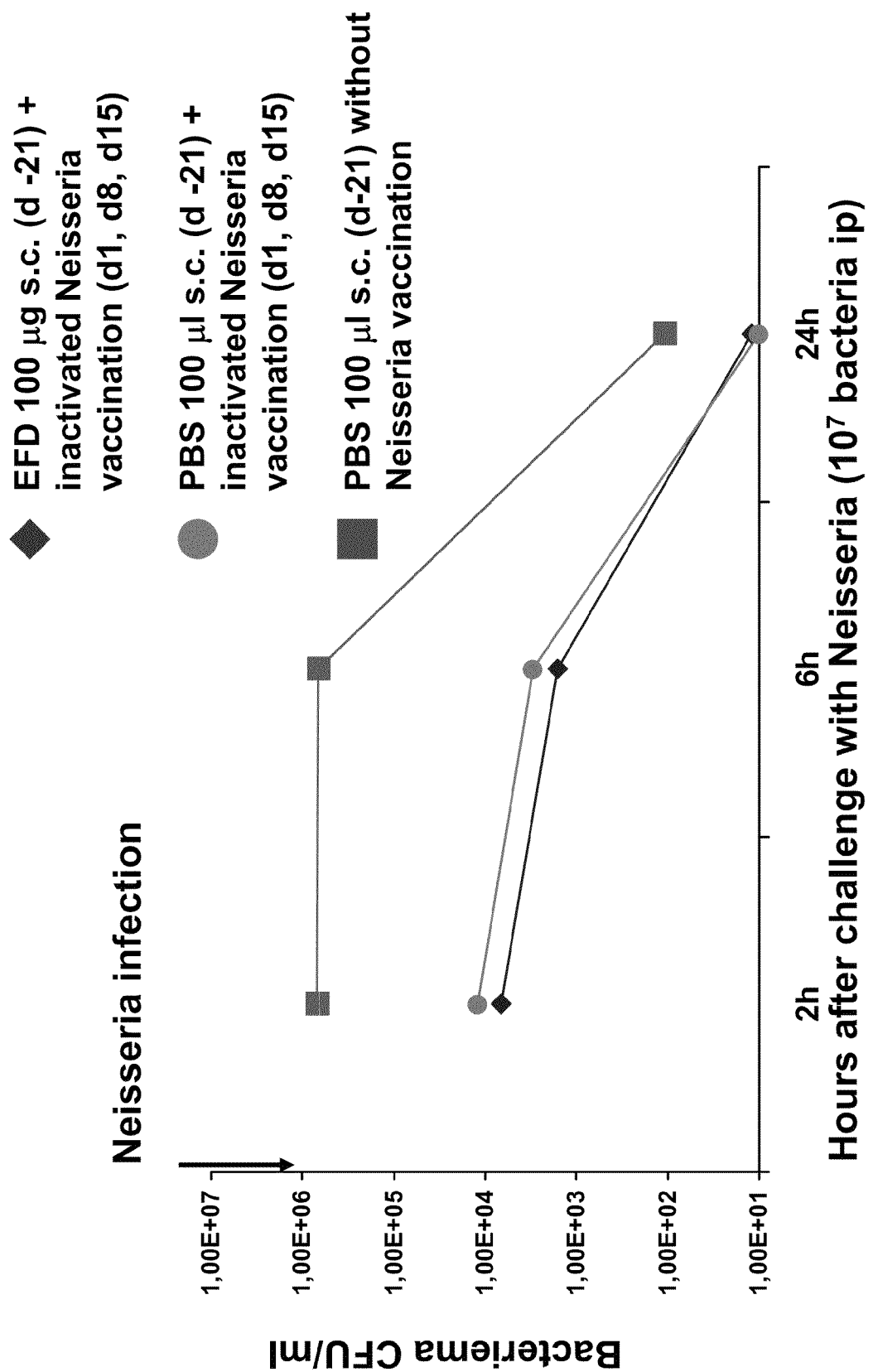

FIG. 31: EFD treatment does not interfere with Neisseria meningitidis vaccination. BALB/C mice were treated with EFD or PBS before Neisseria meningitidis vaccination. Two weeks after the last vaccine injection, vaccinated and non-vaccinated mice were challenged with 10$^7$ CFU of virulent Neisseria meningitidis (ip) and the bacteriemia was measured 2, 6 and 24 hours after the challenge. n=6 mice per group. (♦) EFD 100 μg s.c. (d-21)+inactivated Neisseria vaccination (d1, d8, d15). (●) PBS100 μl s.c. (d-21)+inactivated Neisseria vaccination (d1, d8, d15). (■) PBS100 μl s.c. (d-21) without Neisseria vaccination.

Figure 32:
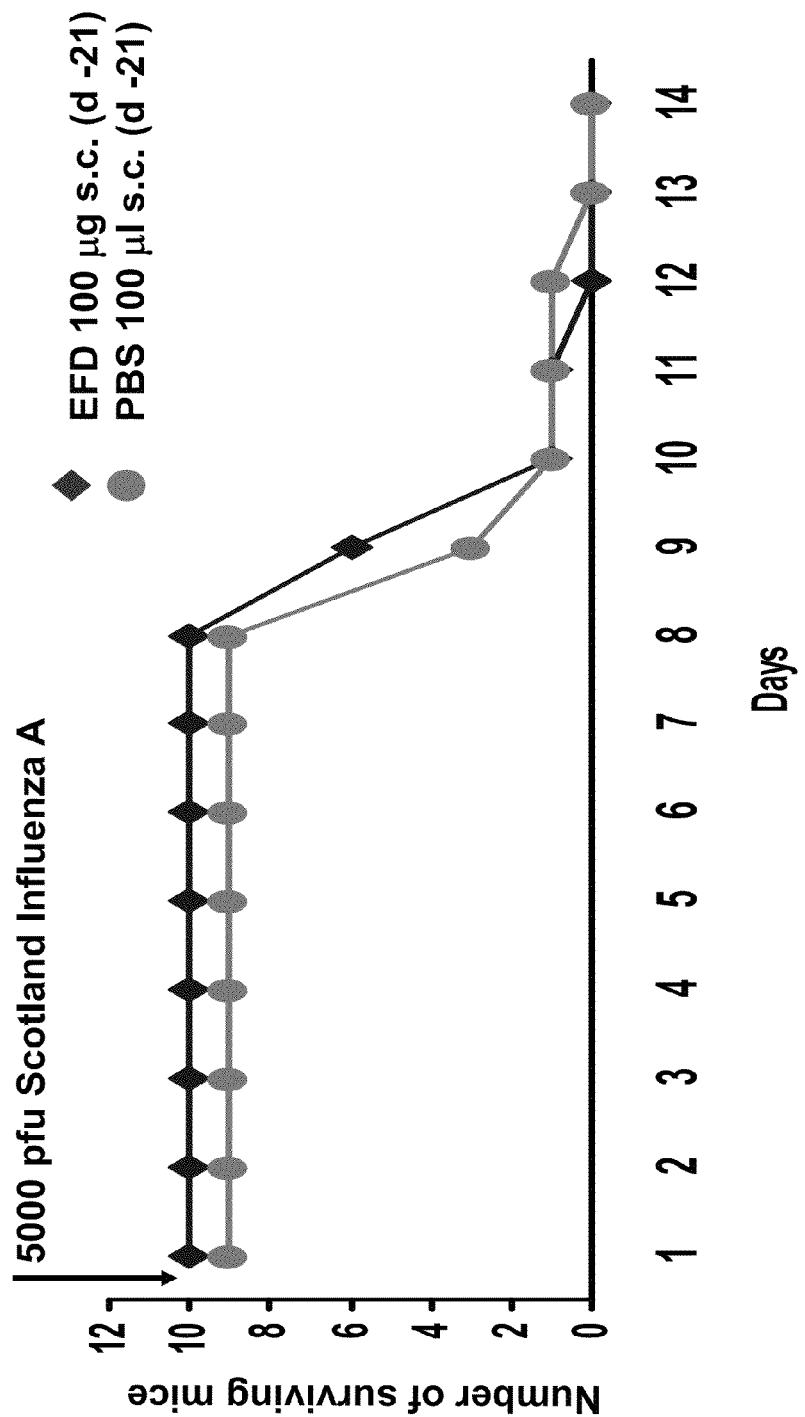

FIG. 32: EFD treatment does not modify the course of influenza virus infection. (♦) BALB/C mice were treated with EFD (100 μg in 100 μl) subcutaneously (s.c.) (d-21). (●) BALB/C mice were treated with PBS (100 μl) subcutaneously (s.c.) (d-21). Twenty-one days later, both groups were intranasally infected with Influenza virus Scotland A strain (5000 pfu), the mice clinical symptoms and the number of surviving mice were daily recorded until day 14.

Figure 33:
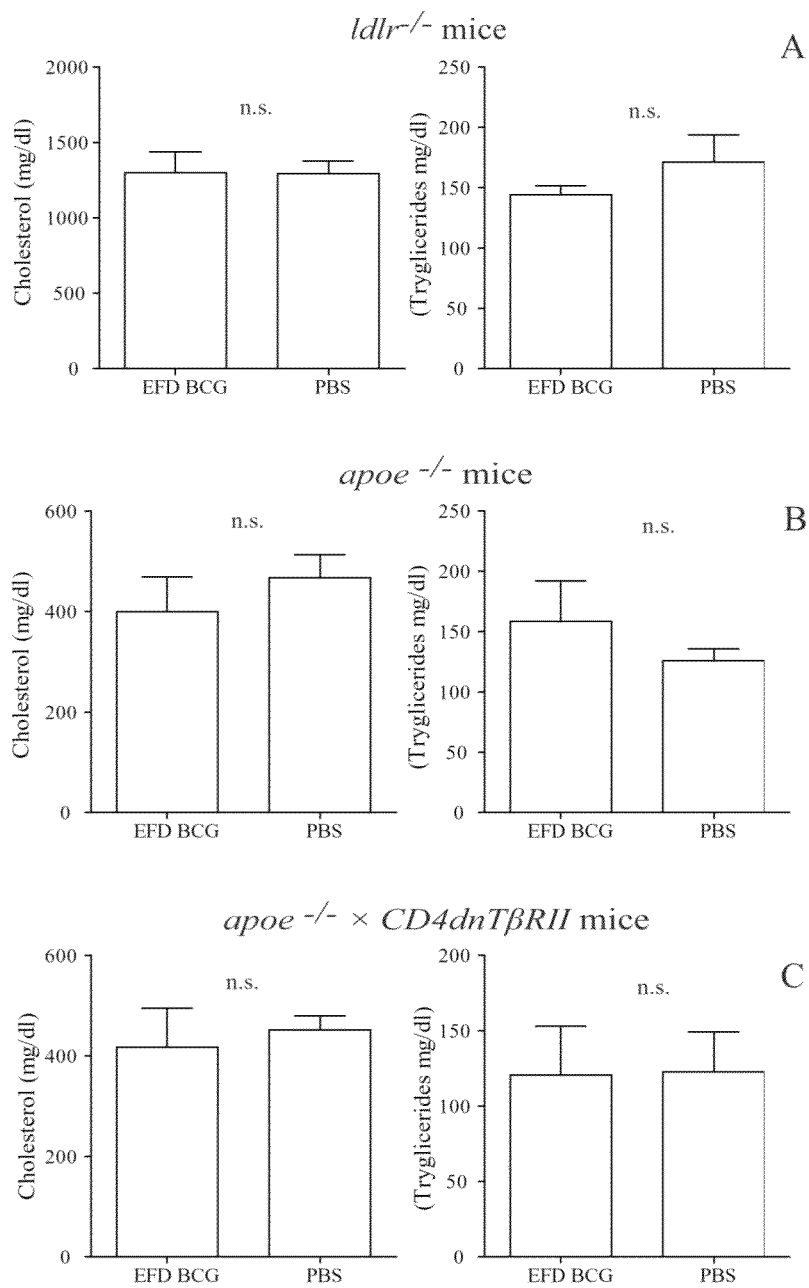

FIG. 33: Lipid Analysis. Levels of total cholesterol and triglycerides were measured in serum of PBS- or EFD BCG-treated mice. (A) Ldlr$^{-/-}$ mice; (B) Apoe$^{-/-}$ mice; and (C) Apoe−/−×CD4dnTβRII mice. Values are expressed as mean±SD (n=4 mice per group). n.s.=not significant.

Figure 34:
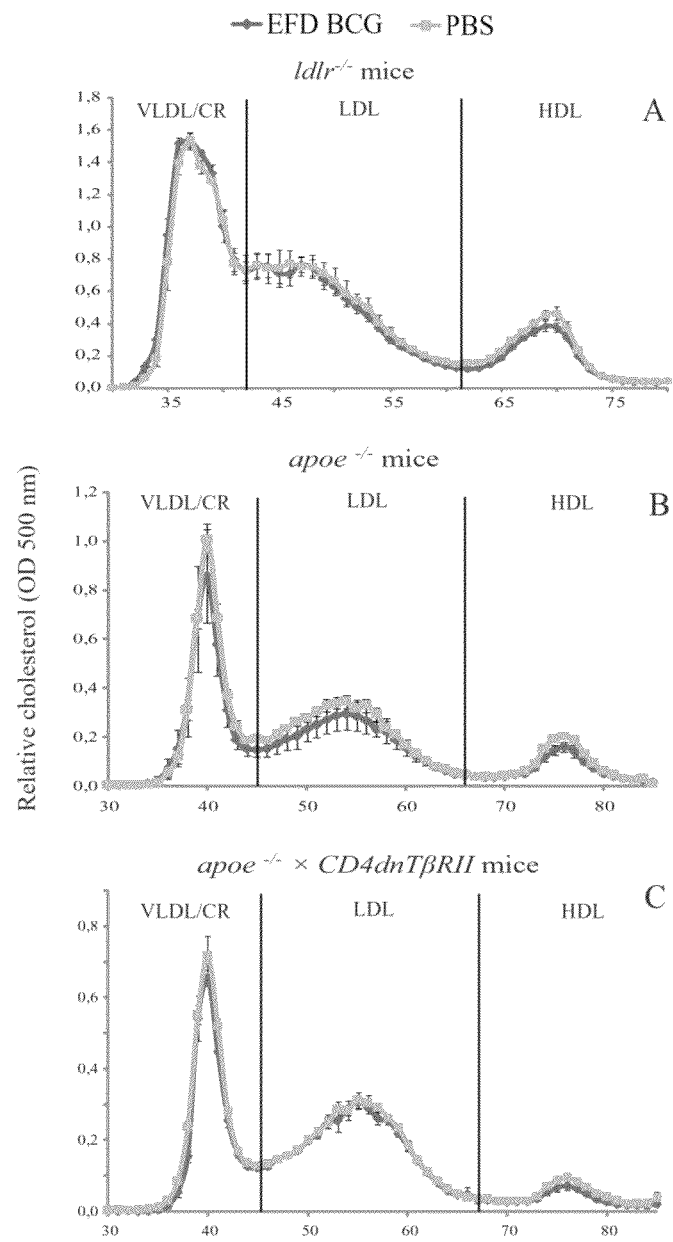

FIG. 34: Cholesterol lipoprotein profiles. Size analysis of lipoprotein profiles from serum of PBS- or EFD BCG-treated mice. Briefly, plasma samples (50 μl) from mice were fractionated on an HR10/30 Superose 6 column (GE HEALTHCARE) and a Discovery BIO GFC-500 as a precolumn (5 cm×7.8 i.d.; Supelco®; SIGMA-ALDRICH), which were coupled to a Prominence UFLC system (SHIMADZU) and equilibrated with Tris-buffered saline, pH 7.4. 200 μl fractions were collected on a Foxy Jr® (TELEDYNE ISCO INC.), and total cholesterol was measured in each fraction using an enzymatic colorimetric kit (RANDOX LAB.). The cholesterol concentration in each fraction (γ axis) is plotted against the retention fraction number (x axis). (A) Ldlr$^{-/-}$ mice; (B) Apoe$^{-/-}$ mice; and (C) Apoe−/−×CD4dnTβRII mice. Curves show mean±SD for EFD BCG-immunized (dark grey lines) and PBS-immunized mice (light gray lines). n=4 mice per group. CR, chylomicron remnants.

Figure 35:
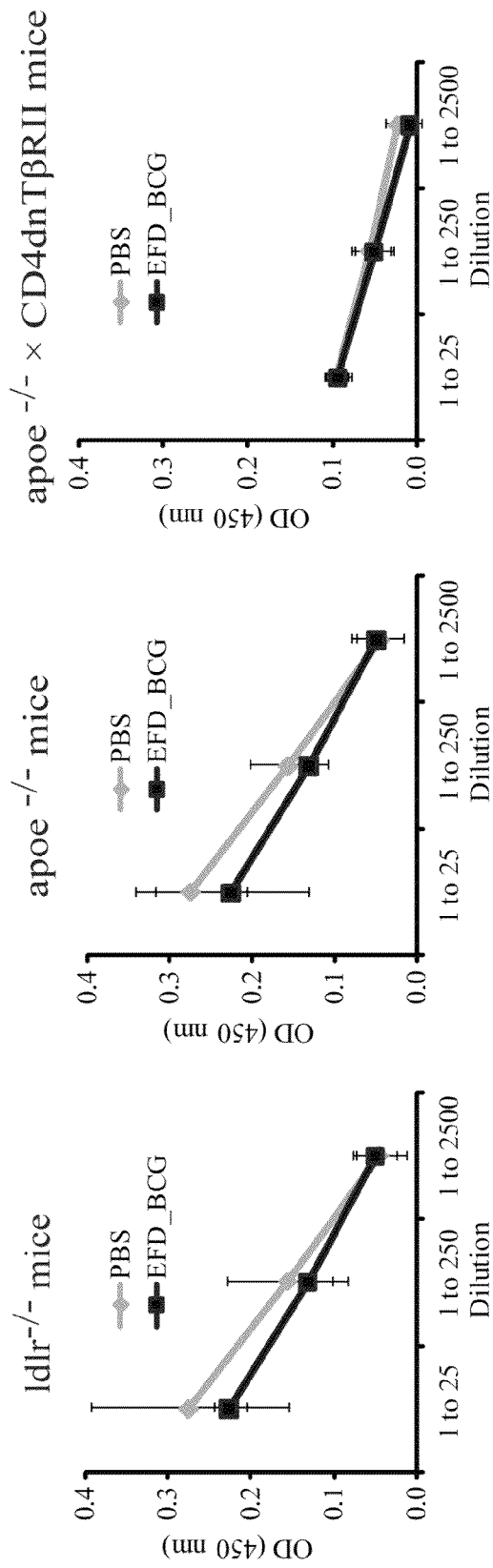

FIG. 35: Antibody titers to oxLDL after EFD BCG treatment. Antibodies to oxLDL in serum of EFD BCG- and PBS-treated mice were measured by ELISA. (A) Ldlr$^{-/-}$ mice; (B) Apoe$^{-/-}$ mice; and (C) Apoe−/−×CD4dnTβRII mice. Curves show mean±SD for EFD BCG-immunized (dark grey lines) and PBS-immunized mice (light gray lines).

n=6 mice per group. Briefly, 50A of the antigens (10 μml in PBS pH 7.4) was added to 96-well ELISA plates and incubated overnight at 4° C. Coated plates were washed with PBS and blocked with 1% gelatin (GIBCO INVITROGEN) in PBS for 1 hr at room temperature. Next, plates were washed and incubated for 2 additional hours with mouse plasma and diluted in Tris-buffered saline (TBS)/gelatin 0.1%. After washing steps, total IgG levels were measured using enzyme-conjugated anti-mouse antibodies (BD BIOSCIENCES). The plates were washed, and colorimetric reactions were developed with TMB (BD BIOSCIENCES). The absorbance was measured on a microplate reader (Versa Max, MOLECULAR DEVICES).

EXAMPLE 1

Preparation of EFD

*Mycobacterium bovis* BCG Pasteur strain (1173P2) killed by extended freeze-drying (EFD) was prepared as described previously in the International PCT Application WO 03/049752. The EFD preparation contained less than 1.5% water at the end of the procedure, as determined with a coulometer by using the Karl-Fischer method (METROHM). Twenty milligrams of EFD was cultured on Middlebrook 7H10 (DIFCO) agar plates to confirm the absence of living bacteria.

The EFD was resuspended in mannitol (5%) at a final concentration of 1 mg/mL, freeze-dried for 72 hours under 0.040 mBar pressure (at this step the aim of the freeze-drying is only to obtain a dry composition) and finally resuspended in distillated water (final concentration of 1 mg/ml) before to be injected to mice.

EXAMPLE 2

Evaluation of EFD Treatment on the Development of Atherosclerosis in ApoE$^{-/-}$ and Ldlr$^{-/-}$ C57Bl/6 mice models 1) Material and methods
a) Experimental Models of Atherosclerosis Induction/Prevention Male ApoE$^{-/-}$ and Ldlr$^{-/-}$ mice were used as two long-term treatment models. Apolipoprotein E deficient (ApoE$^{-/-}$) and low-density lipoprotein receptor-deficient (Ldlr$^{-/-}$) male C57B1/6 mice were bred at the animal care facilities of the INRA campus at Jouy en Josas. Groups of 6-7 mice (5-6 weeks old) at the beginning of the experiment were distributed:

1) ApoE$^{-/-}$ mice from group 1 received three times 100 μl of PBS subcutaneously every 10 weeks (bimonthly) and were sacrificed 2 months after the last injection (34 weeks old).

2) ApoE$^{-/-}$ mice from group 2 received 100 μg of EFD BCG (EFD) subcutaneously at the same intervals than group 1 and were sacrificed 2 months after the third injection of EFD (34 weeks old).

3) ApoE$^{-/-}$ mice from group 3 received 100 μl of PBS subcutaneously every 4 weeks (6 injections at age 6, 10, 14, 18, 22 and 26 weeks) and were sacrificed 1 month after the last injection (30 weeks old).

4) ApoE$^{-/-}$ mice from group 4 received 100 μg of EFD BCG (EFD) subcutaneously at the same intervals than group 3 and were sacrificed 1 month after the sixth injection.

5) Ldlr$^{-/-}$ mice from group 5 received 100 μl of PBS subcutaneously every 4 weeks (6 injections at age 6, 10, 14, 18, 22 and 26 weeks) and were sacrificed 1 month after the last injection (30 weeks old).

6) Ldlr$^{-/-}$ mice from group 6 received 100 μg of EFD BCG (EFD) subcutaneously at the same intervals than group 5 and were sacrificed 1 month after the sixth injection (30 weeks old).

ApoE$^{-/-}$ mice were fed with conventional food whereas Ldlr$^{-/-}$ mice received food supplemented with lipids (15% lard) and 0.5% cholesterol (Genestil), from the first injection of EFD (5-6 weeks old) until the end of the experiment.

b) Flow Cytometric Analysis of Lymphoid Organ Cells

To identify Tregs and dendritic cells (DCs), the inguinal draining lymph nodes (DLNs) of Ldlr-/- mice were harvested 4 days after the first EFD BCG or PBS injection. After collagenase-Dnase digestion, the Draining Lymph Nodes (DLNs) were crushed on a cell strainer to extract the cells that were then stained with antibodies against CD4, CD11c, B220 (BD PHARMINGEN), Foxp3 (EBIOSCIENCES), ICOS, ICOS-L (EBIOSCIENCES), and PDCA-1 (MILTENYI BIOTEC), according to the manufacturer's recommendations.

Splenocytes from ApoE-/- mice were isolated from half of the spleens at week 30 and stained with antibodies against CD4 (BD PHARMINGEN) and Foxp3 (EBIOSCIENCES). All samples were analyzed on a FACSCalibur using CellQuest software (BD BIOSCIENCES).

c) Detection of Transcription Factors in Spleen Cell and Aortic Extracts

The other halves of the spleens (pool of 2 mice) were frozen at −25° C. to be stored during some days. The proteins were extracted from spleens and resolved on 7.5% SDS-PAGE. Protein bands transferred to nitrocellulose sheets were probed with mouse monoclonal anti-FOXP3, -T-bet, -GATA-3, -RORγt, RXRα, p-RXRα, STAT-1, pSTAT-1, STAT-4, p-STAT-4, STAT-5b, p-STAT-5b, STAT-6, p-STAT-6 (SANTA CRUZ BIOTECHNOLOGY) or β-actin mouse monoclonal antibody (Ac-15, ABCAM). Polyclonal goat anti-rabbit (DAKO CYTOMATION) or goat anti-rabbit IgG (SANTA CRUZ BIOTECHNOLOGY), both HRP-conjugated, were used as secondary antibodies. The immune complex was visualized with an enhanced chemiluminescence detection system (AMERSHAM) and scan-analyzed.

Nuclear proteins were extracted from spleen or aortic homogenates (pool of 3 mice) after protease inhibitor treatment and processed with NFκBp65, PPARγ PPAR-α or SP-1 TransAM™ transcription factor assay kits (ACTIVE MOTIF) according to the manufacturer's recommendations. Briefly, 10 μg of nuclear extracts was added to 96-well plates, each plate being coated with a specific oligonucleotide that contained the consensus binding site of the respective transcription factor. Binding was expressed as optical density (OD). The number of treated samples or pools in each experiment is reported in the figure legends.

d) Serological Analysis

Sera were collected from Ldlr-/- at week 30 and from ApoE-/- mice at week 30 or 34. Levels of pro-inflammatory cytokines and chemokines (IL-1α, IL-1β, IL-6, IL-13, IL-17, KC (IL-8), IL-12p40, IL-12p70, IFNγ, TNFα, MIP-1β, Eotaxin) and anti-inflammatory (IL-10) cytokines in the sera were measured using the Bio-Plex cytokine assay (BIO-RAD). TGF-β was measured by ELISA kit (EBIOSCIENCE).

Plasma cholesterol and triglyceride levels of EFD BCG- and PBS-treated mice were measured using enzymatic colorimetric kits (RANDOX LAB.) according to the manufacturer's protocol. Plasma cholesterol lipoprotein profiles were examined using a modified method of Okazaki et al., J. Biochem., 1981, 89, 879-887. Briefly, plasma samples (50 μl) from mice were fractionated on an HR10/30 Superose 6 column (GE HEATHLCARE) and a Discovery BIO GFC-500 as a precolumn (5 cm×7.8 i.d.; Supelco®; SIGMA-ALDRICH), which were coupled to a Prominence UFLC system (SHIMADZU) and equilibrated with Tris-buffered saline, pH 7.4. 200 µl fractions were collected on a Foxy Jr® (TELEDYNE), and total cholesterol was measured in each fraction using an enzymatic colorimetric kit (RANDOX LAB.).

Antibodies to oxLDL in serum of EFD BCG- and PBS-treated mice were measured by ELISA. Briefly, 50 µL of the antigens (10 µg/ml in PBS pH 7.4) was added to 96-well ELISA plates and incubated overnight at 4° C. Coated plates were washed with PBS and blocked with 1% gelatin (GIBCO INVITROGEN) in PBS for 1 hr at room temperature. Next, plates were washed and incubated for 2 additional hours with mouse plasma and diluted in Tris-buffered saline (TBS)/gelatin 0.1%. After washing steps, total IgG levels were measured using enzyme-conjugated anti-mouse antibodies (BD BIOSCIENCES). The plates were washed, and colorimetric reactions were developed with TMB (BD BIOSCIENCES). The absorbance was measured on a microplate reader (VersaMax, MOLECULAR DEVICE).

e) Histological Analysis and Immunostaining of the Atherosclerotic Lesions

Hearts and aorta were collected from EFD-treated and PBS-treated ApoE-/- mice and Ldlr$^{-/-}$ mice and frozen in Optimum Cutting Temperature (OCT; SAKURA FINETEK). The frozen blocks were kept at -80° C. until cryosectioned.

Hearts and ascending aorta of ApoE-/- and Ldlr$^{-/-}$ mice were cryosectioned as previously described (Nicoletti et al., J. Clin. Invest. 1998, 102, 910-918). Ten-micron-thick sections were collected at 100-µm intervals, starting 100 µm from the beginning of the aortic valves. Sections were air-dried and fixed with 4% formaldehyde in PBS and ice-cold acetone for histological and immunohistochemical analysis, respectively. Formaldehyde-fixed sections were stained with hematoxylin and oil red-O or hematoxylin-eosin (HE) and visualized under a light microscope. Areas of the cross-sections of lesions and aorta were quantified using the Leica QWin (LEICA,) and Atherose™ image analysis software programs (MICROVISION INSTRUMENTS). Absolute areas of cross-sections of the lesions were calculated for 8 sections of the aortic root at 100-µm intervals. Comparisons between the groups were made using the mean of the 3 largest sections. Aortic arches of Ldlr$^{-/-}$ mice were cryosectioned. Sections were air-dried and fixed with ice-cold acetone and then hematoxylin-Eosin stained. Lesion area and thickness in three different sites (a, b, c) of the aortic arch was analyzed using Leica QWin image analysis software. The results were expressed as a score (lesion area) for each site. In addition, the mean lesion thickness and surface and mean aortic thickness and surface were calculated from eight to sixteen aorta arch sections of each mouse. Results were expressed as the ratio lesion thickness/aorta thickness, lesion area/aorta area, and as lesion area.

Aortic arches were fixed in 4% formaldehyde, opened longitudinally and stained with Sudan IV (MERCK). Lipid lesions appeared in red.

Immune cells were detected by conventional immunostaining using antibodies against MOMA-2 (macrophages).

f) Statistical Analysis

Data are expressed as mean±SD. The Instat package from Graph Pad Software was used to analyze the data, using the t-test with Welch's correction.

2) Results a) Cytokines and Chemokines in the Sera

Figure 3:
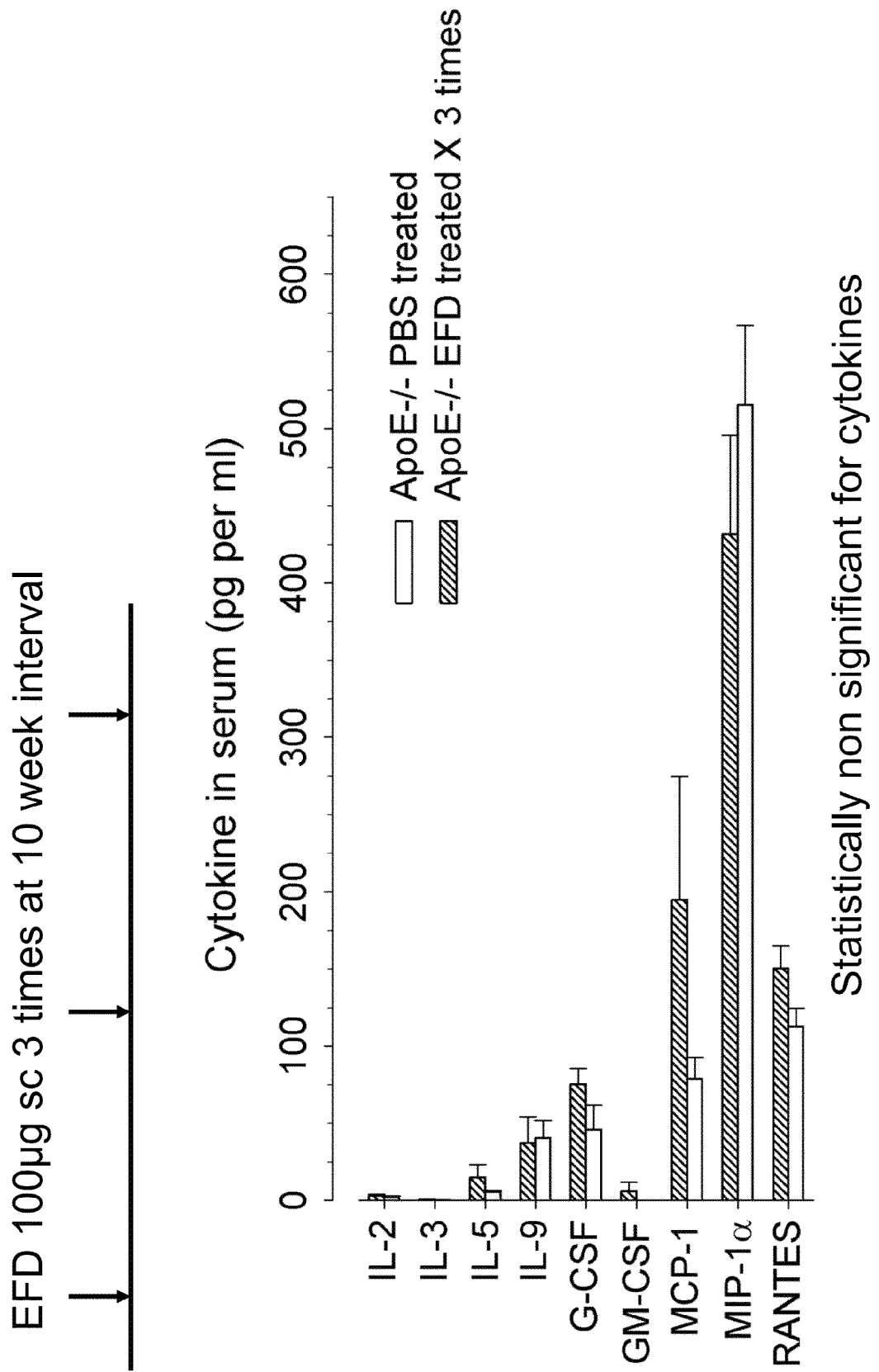
Figure 7:
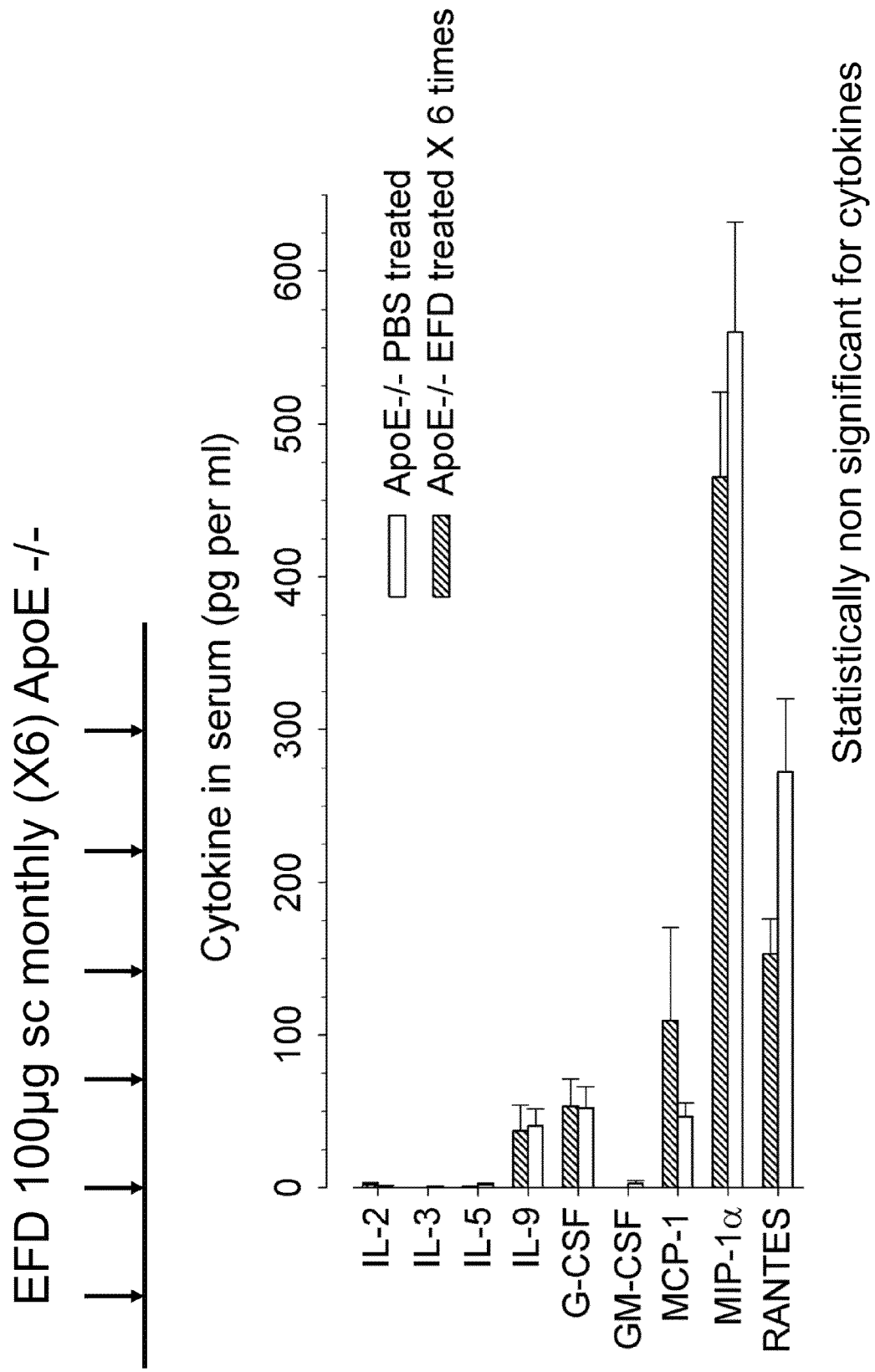

In ApoE$^{-/-}$ mice receiving either 3 or 6 injections of EFD (groups 2 and 4), the serum levels of the anti-inflammatory cytokine IL-10 were significantly increased (8 fold; FIGS. 1, 5 and 11). Concurrently, the serum levels of the inflammatory cytokines and chemokines IL-1α, IL-1β, IL-4, IL-6, IL-12p40, IL-12p70, IL-13, IL-17, Eotaxin, KC (IL-8), MIP-1β and TNF-α but not IFN-γ were significantly decreased as compared to PBS treated mice FIGS. 1, 2, 5, 6 and 11). Serum levels of TGF-β were not significantly increased (2.6-fold) in EFD-treated ApoE$^{-/-}$ mice from group 4 (FIG. 11). The other cytokines and chemokines tested (IL-2, IL-3, IL-5, IL-9, G-CSF, GM-CSF, MCP-1, MIP-1α and RANTES) remained unchanged after EFD treatment (FIGS. 3 and 7).

In Ldlr$^{-/-}$ mice receiving 6 injections of EFD (group 6), the serum levels of IL-10 were increased similarly to what was observed for ApoE$^{-/-}$ (FIGS. 12 and 15). Among the "proinflammatory" cytokines and chemokines tested, IL1-β, MIP1-β, IL-13, KC (IL-8) and TNF-α were significantly reduced and IFN-γ was moderately increased as compared to non-treated mice (FIGS. 13 and 15). TGF-β levels were 1.9-fold increased but not significantly—in the serum of EFD-treated Ldlr$^{-/-}$ mice compared to PBS-treated mice (FIG. 15). It has to be noted that EFD treatment did not significantly reduce IL-6, IL-12p40, IL-17, and Eotaxin in Ldlr-/- mice whereas these cytokines and chemokines were significantly reduced in ApoE$^{-/-}$ mice after 3 or 6 EFD treatments. Other cytokines and chemokines remained unchanged (IL-5, MIP-1α, MIG; FIG. 14).

These data indicate that the administration of EFD BCG to ApoE$^{-/-}$ and Ldlr$^{-/-}$ mice increases systemic IL-10 production and decreases inflammatory cytokine levels (except IFN-γ).

b) Transcription Factors in Spleen Cell and Aortic Extracts

Figure 4:
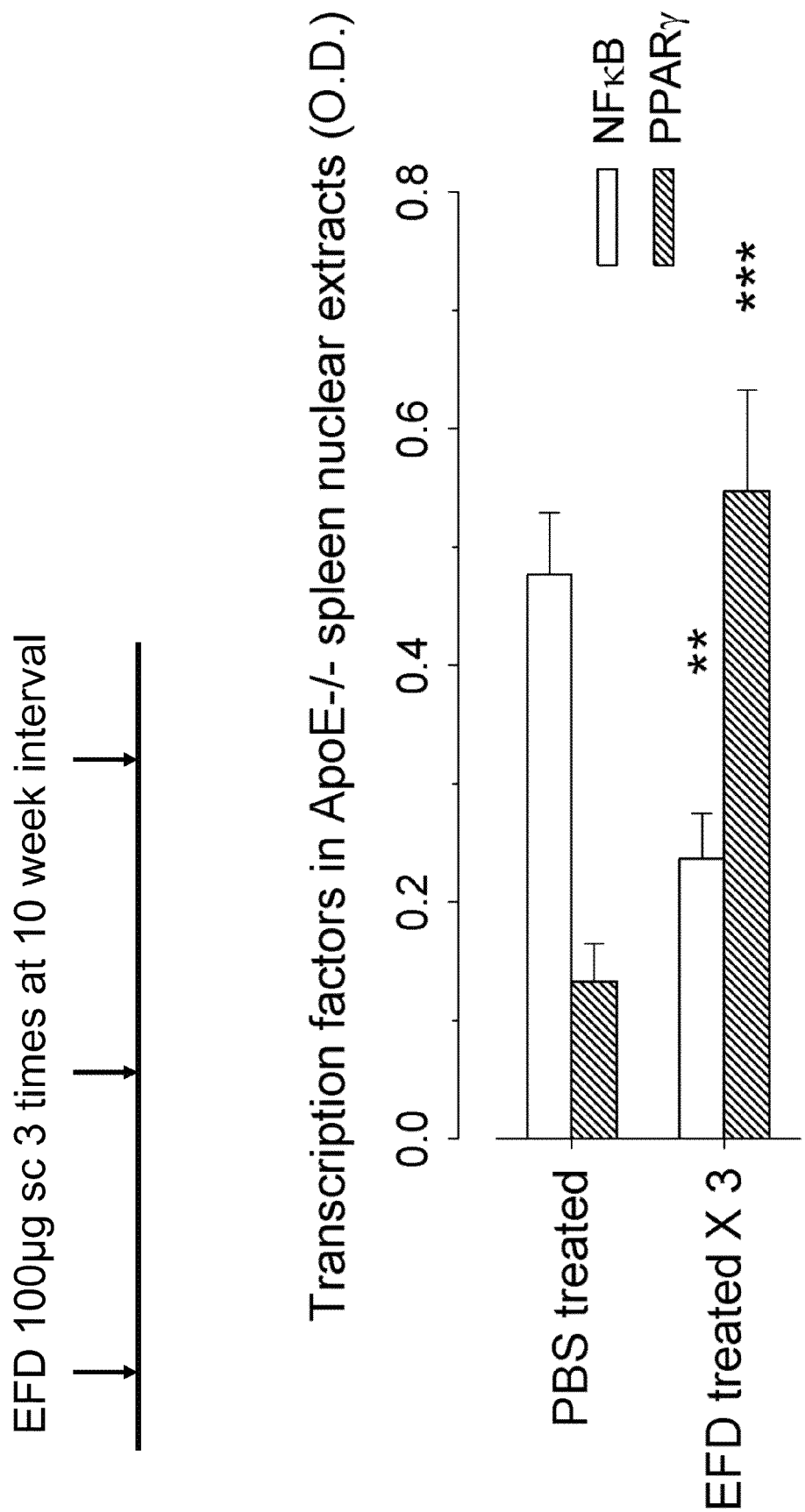

In splenocyte nuclear extracts of ApoE$^{-/-}$ mice receiving 3 or 6 injections of EFD, NFκBp65 was significantly decreased whereas PPARγ expression was enhanced or stabilized (FIGS. 4 and 9).

Figure 8:
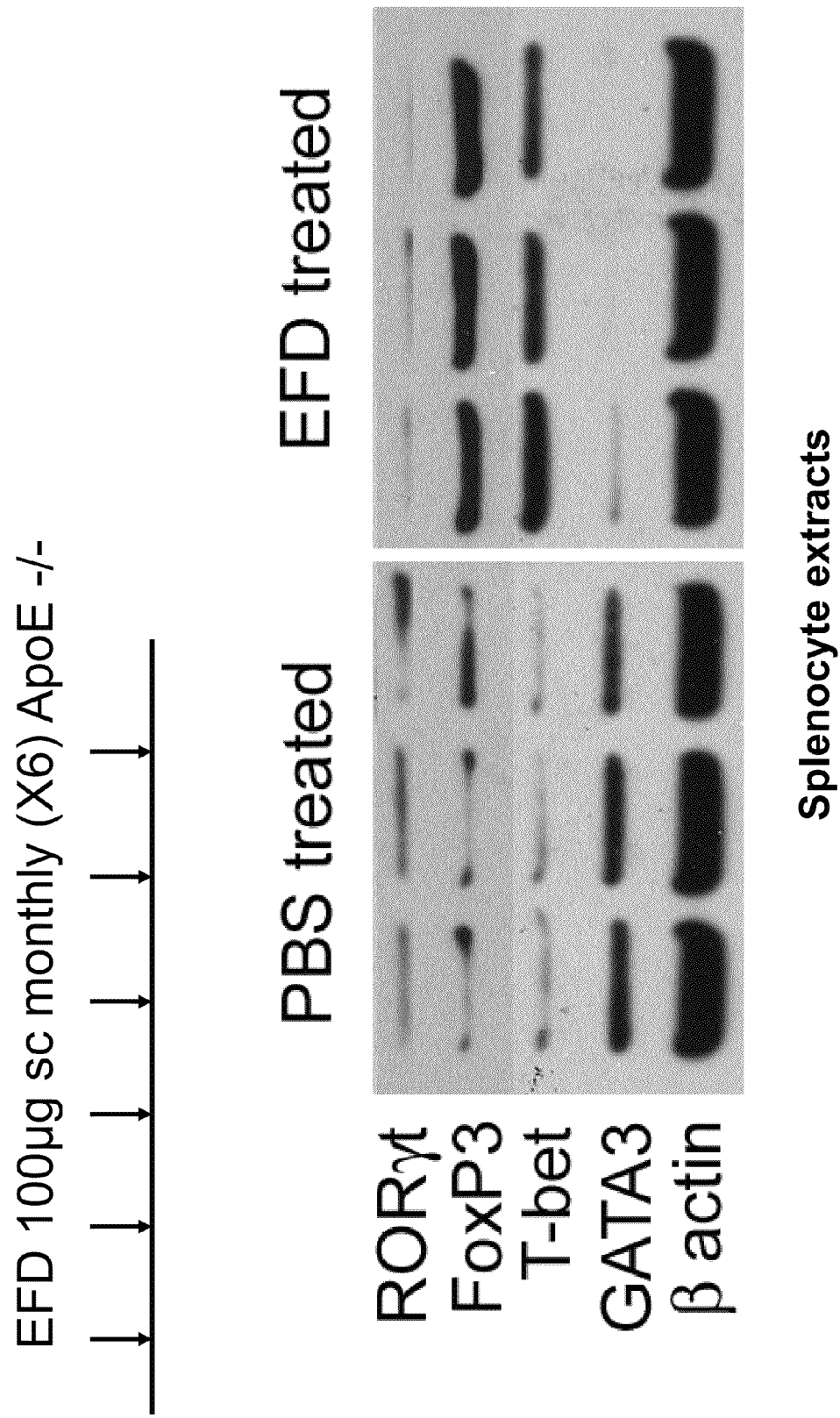

In splenic extracts of ApoE-/- mice receiving 6 injections of EFD, the expression of ROR t (a transcription factor that governs Th17 development (Ivanov et al., Cell, 2006, 126, 1121-1133; signature of inflammatory Th17 cells) and GATA-3 (signature of Th2 cells) fell and the expression of T-bet (a critical transcription factor for Th1 development (Szabo et al., Cell, 2000, 100, 655-669); signature of Th1 cells) and FOXP3 (Treg cells) were strongly enhanced compared with PBS treated ApoE-/- mice (FIG. 8). The SP-1 transcription factor an important component of IL-10-mediated immunoregulation (Chanteux et al., Respiratory Research, 2007, 8, 71-80) was significantly enhanced in spleen nuclear extracts (FIG. 10) in correlation with high levels of IL-10 found in the sera of EFD-treated mice. FACS analysis of spleen cells showed a significantly higher number of CD4+FOXP3+ Treg cells in the EFD-treated mice than in the PBS-treated mice (6 injections) (FIG. 10).

In Ldlr$^{-/-}$ mice, 6 injections of EFD reduced significantly NFκB activation and enhanced PPARγ expression in splenocyte nuclear extracts from 6 mice (FIG. 16B). Similar results were obtained from two extracts of vascular tree tissues of pool of 3 mice (the number of pools was too low to permit a statistical analysis) (FIG. 16A).

To activate transcription, PPARγ requires heterodimerization with the retinoid X receptor α (RXRα), while phosphorylated-RXRα and p-RXRα-PPARγ complex are inactive. In correlation with enhanced PPARγ expression in splenocyte nuclear extracts of EFD treated mice, RXRα expression is enhanced after EFD treatment, associated with a blockage of its phosphorylation, while p-RXRα inactive form was expressed in PBS treated mice (FIG. 18). Moreover, a higher expression of SP-1, transcription factor correlating with IL-10 production, was observed after EFD treatment of Ldlr$^{-/-}$ mice (FIG. 19) as reported previously for ApoE$^{-/-}$ mice (FIG. 10).

Then, the effect of EFD BCG on transcription factors that regulate T cell commitment was determined. EFD treatment was associated with increased T-bet and FOXP3 and decreased RORγt and GATA-3 in splenocyte extracts of Ldlr$^{-/-}$ mice (FIG. 18), as found also in ApoE$^{-/-}$ mice (FIG. 8). EFD treatment correlated with lower phosphorylation of STAT-1, STAT-4, STAT-6, all signatures of Th1 and Th2 inflammatory responses. In addition, STAT-4 is an important factor that regulates Th1 cells development (Thieu et al., Immunity, 2008, 29, 679-690) and p-STAT-4 has recently been shown to impair Treg development (O'Malley JT et al., Immunology, 2009, 127, 587-5953). By contrast, p-STAT-5b, a transcription factor reported to activate Treg response and vascular smooth muscle cells growth (VSMC) was increased (FIG. 17).

Thus, these data indicate that EFD BCG initiates immunoregulatory responses by activating SP-1 and p-STAT-5b, lowering the expression of transcription factors that regulate Th2 and Th17 differentiation, and by increasing the Foxp3$^+$ Treg population. These findings also suggest that EFD BCG has anti-inflammatory effects, as evidenced by decreased phosphorylation of RXRα, STAT-1, STAT-4, and STAT-6; impaired NF-κB activation; and increased PPARγ expression.

c) Plasmacytoid Dendritic Cells (pDCs) and Regulatory T Cells (Tregs)

Because various developmental stages and subsets of Dendritic Cells (DCs) contribute to the expansion and differentiation of T cells that regulate or suppress other immune T cells (Steinman R M et al., Annu. Rev. Immunol., 2003, 21, 685-711), the analysis of DC subsets and Tregs in the inguinal DLNs in Ldlr$^{-/-}$ mice was performed. EFD treatment induced the recruitment of plasmacytoid dendritic cells (pDCs). Four days after the first subcutaneous injection of 100 mg of EFD, more plasmocytoid DCs (pDCs; CD11clow B220high) were detected in the draining lymph nodes of EFD BCG compared with PBS injected mice (15% versus 0.3% of gated CD11c+ cells; FIG. 20). In contrast, fewer conventional DCs (cDCs; CD11chigh B220neg) were observed in the DLNs after EFD BCG injection compared with PBS (32% versus 83% of gated CD11c+ cells; FIG. 20). Moreover, 99% to 100% of the pDCs (CD11c$^{low}$B220$^{hi}$) that homed to the inguinal DLNs after EFD BCG or PBS injection expressed PDCA-1, a marker of mouse pDCs (Asselin et al., J. Immunol., 2003, 171, 6466-6477).

Maturing pDCs can generate Tregs by expressing high levels of inducible costimulatory ligand (ICOS-L) (Ito T, et al., J. Exp. Med., 2007, 204, 105-115). More ICOS-L-expressing pDCs in the inguinal DLNs of Ldlr-/- mice were detected after EFD BCG injection than after PBS treatment (8% versus 0.7% of gated CD11c,) and in absolute number 38529±1906 versus 415±48, P<0.001; FIG. 22A). In parallel, the percentage of CD4$^+$Foxp3$^+$ Tregs in the inguinal DLNs of EFD BCG-treated mice rose compared with control mice (13.2% versus 5.5% of gated CD4$^+$ cells; FIG. 21). As ICOS expression has been implicated in the reduction of atherosclerosis (Gotsman et al., Circulation, 2006, 114, 2047-2055), the number of ICOS$^+$ Tregs induced by EFD-BCG was measured. CD4$^+$Foxp3$^+$ICOS$^+$ cells were much more numerous in the inguinal lymph node after EFD-BCG than after PBS injection (119091±5890 versus 22814±2626, P<0.001; FIG. 22B).

d) Atherosclerotic Lesions

The effect of EFD BCG on the development of atherosclerosis in ApoE$^{-/-}$ and Ldlr$^{-/-}$ mice was determined.

After EFD BCG treatment (6 injections) of ApoE$^{-/-}$ mice, mean cross-sectional area of atherosclerotic lesions in the aortic root was significantly lower compared with the control (59442±24695 μm2 versus 92502±43607 μm2; FIG. 23A), as was macrophage accumulation (MOMA-2$^+$ cells) (FIG. 23B).

Administration of EFD BCG to Ldlr$^{-/-}$ mice reduced the size of the atherosclerotic lesions (Table I, FIGS. 24, 25 and 26).

Table I illustrates a semi-quantification of the atherosclerotic lesion area in three different sites (a, b or c) of the aortic arch (FIG. 24), for each Ldlr$^{-/-}$ mice of the PBS-treated group (6 mice) and each Ldlr$^{-/-}$ mice of the EFD-treated group (6 mice). The mean value at each site is also indicated for the PBS-treated and EFD-treated groups (Table I).

TABLE I

Quantification of atherosclerotic lesions in different sites of the aortic arch

| PBS-treated mice | Lesion area (arbitrary units) in different sites of aortic arch | | | EFD-treated mice | Lesion area (arbitrary units) in different sites of aortic arch | | |
| --- | --- | --- | --- | --- | --- | --- | --- |
| | a | b | c | | a | b | c |
| N°1 | 3 | 3 | ND | N°1 | 2 | — | ND |
| N°2 | 0.5 | ND | 2 | N°2 | 2 | 3 | 3 |
| N°3 | 4 | 4 | 1 | N°3 | 2 | 2 | 1 |
| N°4 | 3 | 4 | 4 | N°4 | 3 | 2 | 1 |
| N°5 | ND | 4 | 4 | N°5 | 3 | 2 | 1 |
| N°6 | 4 | 3 | 3 | N°6 | 2 | 1 | ND |
| mean | 2.9 | 3.6 | 2.8 | mean | 2.4 | 1.6 | 1.5 |

* ND: non-determined

In the EFD treated mice, the lesions were statistically smaller in site b (p=0.015; Mann-Whitney test).

The quantification of the lesion area and thickness in the 6 EFD-treated and PBS-treated Ldlr$^{-/-}$ mice (FIGS. 25 and 26) demonstrated that the lesion area and thickness were significantly reduced in the EFD-treated Ldlr$^{-/-}$ mice.

Administration of EFD BCG to Ldlr-/- mice reduced lesional cross-section area in the aortic root compared to PBS-treated mice (87072±28079 μm$^2$ versus 204051±73623 μm$^2$, P<0.01; FIG. 27A) and decreased lipid lesion area in the en face aortic preparation as shown in FIG. 27B.

Immunohistochemistry showed less infiltration of MOMA2$^+$ macrophages in cross-sectional atherosclerotic lesions in EFD BCG-compared with PBS-treated mice (P<0.01; FIGS. 27C and D), what may also prevent plaque rupture, the highest danger in atherosclerotic disease.

e) Lipid Profiles and Antibody Titers to Oxidized LDL (ox-LDL)

Serum cholesterol, triglycerides, and cholesterol lipid profiles were unchanged after EFD BCG treatment (FIGS. 33 and 34).

In addition, levels of antibodies to serum oxLDL did not differ between EFD BCG- and PBS-treated mice, suggesting that EFD BCG protection is independent of an atherosclerotis-specific antigen (FIG. 35).

EXAMPLE 3

Evaluation of EFD BCG Treatment on the Development of Atherosclerosis in ApoE$^{-/-}$×CD4dnTβRII Mice Model

1) Material and Methods

Female ApoE−/−×CD4dnTβRII mice on the C57BL/6J background, which express dominant-negative TGF-β receptor II under the CD4 promoter (Robertson et al., J. Clin. Invest., 2003, 112, 1342-1350), were used as a short-term model of atherosclerosis. They were generated and housed in the breeding facilities at Karolinska University Hospital with permission from the Stockholm County Regional Ethical Committee. These mice received 2 subcutaneous injections at the base of the tail with 100 μl PBS or 100 μg EFD BCG at age 6 and 9 weeks. They were fed standard chow and sacrificed at age 12 weeks. The cytokine and transcription factor analysis and the immunohistochemical studies were performed as described in example 2.

2) Results

TGF-β can be produced by Tregs and reduces the development of atherosclerosis by inhibiting T cell activation (Gojova et al., Blood, 2003, 102, 4052-4058; Robertson et al., J. Clin. Invest., 2003, 112, 1342-1350; Ait-Oufella et al., Nat. Med. 2006, 12, 178-180). As a tendency for increased levels of TGF-β in the serum of EFD BCG-treated mice was observed (FIGS. 11 and 15), the effect of EFD BCG in Apoe−/−×CD4dnTβRII mice was examined.

Despite the short treatment with EFD BCG, the size of atherosclerotic lesions in the aortic root was reduced by 30% compared with PBS (193600±85948 μm2 versus 278086±87089 μm2, P<0.05; FIG. 28A, B).

In conventional models of atherosclerosis (Ldlr−/− and Apoe−/−) EFD BCG increases respectively 4- to 8-fold IL-10 production, and 16-fold in EFD BCG-Apoe−/−×CD4dnTβRII mice versus untreated mice (P<0.001; FIG. 28C). Serum TNF-α levels declined slightly in EFD BCG-treated mice compared with PBS-treated mice (FIG. 28C), while IFN-γ, IL-4, IL-5, IL-13, and IL-17 serum levels did not differ between the 2 groups. Notably, EFD BCG enhanced Foxp3 protein expression in splenocyte extracts of Apoe−/−×CD4dnTβRII mice (FIG. 28D).

These results suggest that EFD BCG reduces atherosclerosis by promoting Treg expansion and IL-10 production in the absence of TGF-β signaling.

EXAMPLE 4

EFD BCG Treatment has No Measurable Toxicological Side Effects

1) Materials and Methods

Female OF1 Swiss mice, which are typically used in toxicology studies, were housed in the animal experimentation unit of Institut Pasteur and injected for 14 consecutive days with 100 μl PBS or 0.01, 0.1, or 1 mg EFD BCG (10 mice per group). The body weight and rectal temperature were measured every day, 24 hours after each injection as previously described (Lagranderie et al., J. Allergy Clin. Immunol., 2008, 121, 471-478). Twenty-four hours after the last injection, the mice were sacrificed, and the spleens were recovered for nuclear PPARγ and PPARα measurements as described in example 2.

2) Results

Multiple Injections of EFD do not Induce Measurable Side Effects

The side effects of repeated treatment with EFD BCG was evaluated in OF1 outbred Swiss mice that are highly diverse on a population level and often used in toxicological studies. After 14 consecutive injections of various doses of EFD BCG (0.01, 0.1, 1 mg), as compared to PBS-treated mice no change of rectal temperature was observed (FIG. 29A). Body weight of EFD BCG- and PBS-treated mice increased similarly (6% to 7%) from Days 0 to 14 (FIG. 29B).

Finally, we also showed that EFD BCG treatment enhanced PPARγ expression without affecting PPARα expression. Indeed the combination of PPARγ agonists (used as insulin sensitizers in diabetic patients who are at high risk for cardiovascular disease) and of PPARα agonists (used to treat dyslipidemia) enhanced atherosclerosis in ApoE−/− (Calkin et al., Atherosclerosis, 2007, 195, 17-22) and induced major adverse cardiovascular events in humans (Nissen et al., JAMA, 2005, 294, 2581-2586).

Therefore, the expression of two PPAR isoforms (α and γ) was measured in splenocyte extracts from OF1 Swiss mice that received increasing doses of EFD BCG for 14 consecutive days. Compared with PBS-injected mice, PPARγ expression increased after EFD BCG injection dose-dependently, whereas PPARα levels remained identical, even at the highest doses of EFD BCG (FIG. 29C). That EFD BCG is a selective inducer of PPARγ and does not induce PPARα activation, is an advantage, supporting its potential for clinical use in human beings.

EXAMPLE 5

EFD Treatment does not Interfere with *M. tuberculosis*, *Leishmania major* or Influenza Virus Infections or Impair BCG or *Neisseria* Vaccination Finally, the effects of EFD BCG on host defense capacity was assessed a) *M. tuberculosis* Infection and BCG Vaccination Guinea-pigs, a species more susceptible to *M. tuberculosis* than mice, were injected with:
- Group 1: PBS (100 μl) on day 0 (control)
- Group 2: BCG (10$^6$ colony forming units (CFU) in 100 μl PBS) on day 0
- Group 3: BCG (10$^6$ colony forming units (CFU) in 100 μl PBS) on day 42
- Group 4: EFD ((100 μg) in 100 μl of PBS) on day 0
- Group 5: EFD ((100 μg) in 100 μl of PBS) on day 0 and BCG (10$^6$ colony forming units (CFU) in 100 μl PBS) on day 42
- Group 6: BCG (10$^6$ colony forming units (CFU) in 100 μl PBS) on day 0 and EFD ((100 μg) in 100 μl of PBS) on day 42.

On day 80, all the groups (n=6 guinea-pigs per group) were challenged with *Mycobacterium tuberculosis* (H37Rv; 5.10$^5$ CFU). The guinea pigs were sacrificed at day 122. The spleens were collected and homogenized. Appropriate dilutions for homogenized spleens were plated on Middlebrook 7H10 agar medium (DIFCO). The plates were incubated at 37° C. for one month and the colony forming units (CFUs) of virulent bacteria were counted.

EFD treatment, before or after BCG vaccination or without BCG vaccination, did not sensitize to *M. tuberculosis* infection or impair BCG vaccination (FIG. 30).

b) *Leishmania major* Infection Assay

BALB/c mice (non healer mice) and C57B1/6 mice (healer mice), 8 per group, were injected (Day 0) at the base of the tail with: 100 µl of PBS or EFD (100 µg) in 100 µl of PBS. On day 45, they received 10 to 20 viable *Leishmania major* parasites in 10 µl, in right ear.

Local inflammations were observed and measured during 6 months: no differences were observed between PBS and EFD treated groups.

Metastatic lesions were recorded on day 160.

In the PBS-treated group, all mice (except one) had small to medium local lesions: 5 had normal tail, 1 with small lesion at the base of the tail and 2 had lost their tail and they had lesion on rear footpads.

In the EFD-treated group, all mice had small to medium local lesions: 7 had their tail, 2 with a small lesion at the base of the tail and 1 had lost its tail, with lesions on both rear footpads. No differences (similar lesions) were observed between PBS and EFD treated groups of BALB/c mice (non healer mice). No differences (absence of lesion on all mice) were observed between PBS and EFD injected C57B1/6 mice (healer mice).

These results which show that EFD treatment does not sensitize the mice to *Leishmania major* infection indicate that EFD does not interfere with pathogen infection.

c) *Neisseria* Vaccination

One group of BALB/c mice was treated subcutaneously with 100 µg of EFD in 100 µl, the two other groups received 100 µl of PBS (n=6 mice per group). Twenty-one days later, the EFD-treated group and one of the PBS-treated group were vaccinated with heat-killed *Nesseiria meningitidis* (3 doses at one week interval). The second group of PBS-injected mice was not vaccinated (control). Two weeks after the last vaccine injection, vaccinated and non-vaccinated mice were challenged with $10^7$ CFU of virulent *Neisseria meningitidis* (ip) and the bacteriemia was measured 2, 6 and 24 hours after the challenge. EFD treatment did not modify the protective effect of the vaccination (FIG. 31).

d) Influenza Virus Infection

One group of BALB/c mice was treated subcutaneously with 100 µg of EFD in 100 µl, the other group received 100 µl of PBS. Twenty-one days later, both groups were intranasally infected with Influenza virus Scotland A strain (5000 pfu), the mice clinical symptoms and the number of surviving mice were daily recorded for 14 days. No difference was found between EFD-treated and PBS-treated groups (FIG. 32), indicating that EFD treatment does not modify the course of influenza virus infection.

These data demonstrate that despite its immunoregulatory effects, EFD BCG did not attenuate the protection that was conferred by vaccines against *Mycobacterium tuberculosis* in guinea pigs, *Neisseria meningitidis* in mice (infections that induce Th1- and Th2-mediated immune responses, respectively), nor did it exacerbate *Mycobacterium tuberculosis* infection in guinea pigs and influenza virus or *Leishmania major* infections in mice. Thus, EFD BCG does not cause any measurable adverse effects in two animal species, in different mouse strains, and when given at high doses.

CONCLUSIONS FROM EXAMPLES 1 TO 5

The present studies demonstrate that EFD BCG exerts protective effects against the development of atherosclerosis in 3 distinct mouse models. EFD BCG elicited simultaneously: 1) an immunoregulatory effect through IL-10 production and expansion of Tregs, 2) an inhibition of NF-κB activation, and 3) an increase in PPARγ without altering PPARα levels. EFD BCG had no measurable side effects in this study, and despite its immunoregulatory activity, it did not attenuate protection conferred by vaccines generating Th1 and Th2 immune responses, nor did it exacerbate *M. tuberculosis* infection.

In all models, EFD BCG significantly reduced the size of atherosclerotic lesions and induced IL-10 production. Furthermore in Ldlr-/- mice, EFD BCG treatment increased the number of plasmacytoid dendritic cells (pDCs) and Foxp3$^+$ Tregs in the draining lymph nodes shortly after injection. At the end of the experiment, Treg accumulation in the spleen, decreased serum levels of proinflammatory cytokines, reduced NF-κB, and increased PPARγ expression in spleen and vascular nuclear extracts were observed in Ldlr-/- mice. Elevated serum levels of IL-10 in EFD BCG-treated Ldlr-/- mice were accompanied by increased expression of transcription factors that govern the activation of IL-10 (SP-1 and p-STAT5b) in spleen extracts, supporting the notion that IL-10 mediates atheroprotection. In addition to enhancing IL-10 signaling, long-term treatment with EFD BCG in Ldlr-/- and ApoE-/- mice decreased most of the inflammatory cytokines that we tested, except IFN-γ. The concomitant reduction in nuclear NF-κB and augmentation of PPARγ in Ldlr-/- mice, associated with reduced phosphorylated RXR-levels, suggests that EFD BCG robustly inhibits the inflammatory state. The expression profile of transcription factors and cytokines reflected downregulation of Th2 differentiation by EFD BCG, as evidenced by lower serum levels of IL-13 and decreased GATA3 and p-STAT-6 in the spleen. The pattern was less apparent with regard to the Th1 arm. Indeed, EFD BCG triggered higher levels of IFN-γ, the Th1 cytokine signature, in the serum of Ldlr-/- and ApoE-/- mice, and enhanced, in spleen cell extracts, T-bet expression, a critical transcription factor for Th1 development. However, EFD BCG lowered the phosphorylation of STAT-4, another important factor that regulates Th1 cells development. Because p-STAT-4 has recently been shown to impair Treg development, the reduction of p-STAT-4 induced by EFD BCG potentially benefited Treg expansion in this study. Finally, the role of Th17 cells was examined by studying RORγt, a transcription factor that governs Th17 cell development. RORγt levels were lower after EFD BCG treatment in Ldlr-/- and Apoe-/- mice, concomitant with decreased levels of IL-17 in the latter model. The partial modulation of the Th1 arm of immunity associated to a reduced Th17 and a stronger Treg profiles may be sufficient to protect against atherosclerosis while maintaining an efficient immunocompetence of the host, as attested by the unaltered immune defense against *Mycobacterium tuberculosis* and *Neisseria meningitidis* in EFD BCG treated mice. The modulated systemic inflammatory profile in the EFD BCG-treated mice was also associated to a reduced local accumulation of MOMA$^+$ macrophages in the lesions (FIGS. 23B, 27C and 27D), what may also prevent plaque rupture, the highest danger in atherosclerotic disease. After EFD BCG immunization, no evidence for immunosuppression was observed as assessed by reactivity to *M. tuberculosis* (Th1 mediated protection) or *N. meningitidis* (Th2 mediated protection). The maintenance of immunocompetence against infections after EFD BCG treatment suggested that it is a tolerable therapeutic agent in humans. Finally, EFD BCG is a selective inducer of PPARγ and does not induce PPARα activation, which is an advantage, supporting its potential for clinical use. In conclusion, EFD BCG is a promising candidate as an immunotherapeutic preparation for prevention and treatment of atherosclerosis.

The invention claimed is:

1. A method for the prophylactic or curative treatment of atherosclerosis, comprising the step of administering to a patient an effective amount of a composition comprising killed *Mycobacterium bovis* BCG bacteria which are killed by extended freeze-drying, which are obtained by a process comprising:
   (i) harvesting a culture of living *Mycobacterium bovis* BCG bacteria cells,
   (ii) freezing the *Mycobacterium bovis* BCG bacteria cells in water or in an aqueous solution of salt,
   (iii) killing the frozen *Mycobacterium bovis* BCG bacteria cells by drying them in a lyophilizer, for a time sufficient to remove at least 98.5% of the water, and
   (iv) collecting the extended freeze-dried killed *Mycobacterium bovis* BCG bacteria cells.

2. The method according to claim 1, wherein said killed *Mycobacterium bovis* BCG bacteria are non-denatured.

3. The method according to claim 2, wherein said killed and non-denatured *Mycobacterium bovis* BCG bacteria comprise proteins whose primary structure is preserved.

4. The method according to claim 1, wherein said killed *Mycobacterium bovis* BCG bacteria consist of killed and non-denatured *Mycobacterium bovis* BCG bacteria and less than 1.5% of water.

5. The method according to claim 1, wherein said composition comprises from about 10 µg to about 10 mg of said killed *Mycobacterium bovis* BCG.

6. The method according to claim 5, wherein said composition comprises from about 100 µg to about 1 mg of said killed *Mycobacterium bovis* BCG bacteria.

7. The method according to claim 5, wherein said composition comprises 100 µg of said killed *Mycobacterium bovis* BCG bacteria, and wherein said composition is administered subcutaneously every week.

8. The method according to claim 5, wherein said composition comprises 100 µg of said killed *Mycobacterium bovis* BCG bacteria, and wherein said composition is administered subcutaneously every month.

9. The method according to claim 5, wherein said composition comprises 100 µg of said killed *Mycobacterium bovis* BCG bacteria, and wherein said composition is administered subcutaneously every 3 to 6 months.

10. The method according to claim 1, wherein said composition is administered, simultaneously, separately or sequentially with one or more of an anti-inflammatory and an immunomodulatory drug.

* * * * *